(12) United States Patent
Iwabuchi et al.

(10) Patent No.: US 8,871,981 B2
(45) Date of Patent: Oct. 28, 2014

(54) METHOD FOR OXIDIZING ALCOHOLS

(75) Inventors: Yoshiharu Iwabuchi, Miyagi (JP);
Masaki Hayashi, Miyagi (JP)

(73) Assignee: Tohoku University, Miyagi (JP)

( * ) Notice: Subject to any disclaimer, the term of this patent is extended or adjusted under 35 U.S.C. 154(b) by 113 days.

(21) Appl. No.: 13/809,753

(22) PCT Filed: May 30, 2011

(86) PCT No.: PCT/JP2011/062324
§ 371 (c)(1),
(2), (4) Date: Mar. 14, 2013

(87) PCT Pub. No.: WO2012/008228
PCT Pub. Date: Jan. 19, 2012

(65) Prior Publication Data
US 2013/0172543 A1 Jul. 4, 2013

(30) Foreign Application Priority Data

Jul. 16, 2010 (JP) ................................. 2010-161268

(51) Int. Cl.

| | | |
|---|---|---|
| *C07C 45/29* | (2006.01) | |
| *C07D 493/20* | (2006.01) | |
| *C07D 213/50* | (2006.01) | |
| *C07H 19/16* | (2006.01) | |
| *C07C 269/06* | (2006.01) | |
| *C07C 45/39* | (2006.01) | |
| *C07C 201/12* | (2006.01) | |
| *C07H 9/04* | (2006.01) | |
| *C07C 45/30* | (2006.01) | |
| *C07B 53/00* | (2006.01) | |
| *C07H 19/167* | (2006.01) | |

(52) U.S. Cl.
CPC .............. *C07H 19/16* (2013.01); *C07C 269/06* (2013.01); *C07C 45/39* (2013.01); *C07C 45/29* (2013.01); *C07C 201/12* (2013.01); *C07H 9/04* (2013.01); *C07C 45/30* (2013.01); *C07B 53/00* (2013.01); *C07D 213/50* (2013.01); *C07D 493/20* (2013.01); *C07B 2200/07* (2013.01); *C07C 2101/14* (2013.01); *C07H 19/167* (2013.01); *C07C 2103/74* (2013.01)
USPC ........... 568/322; 568/339; 568/361; 568/436; 549/334; 546/314; 536/27.6

(58) Field of Classification Search
USPC .................. 568/322, 339, 361, 436; 549/334; 546/314; 536/27.6
See application file for complete search history.

(56) References Cited

U.S. PATENT DOCUMENTS

| | | |
|---|---|---|
| 2007/0232838 A1 | 10/2007 | Iwabuchi et al. |
| 2009/0124806 A1 | 5/2009 | Iwabuchi et al. |
| 2010/0282422 A1 | 11/2010 | Miyawaki et al. |

FOREIGN PATENT DOCUMENTS

| | | |
|---|---|---|
| FR | 2219159 | 9/1974 |
| JP | 2008-212853 | 9/2008 |
| JP | 2009-114143 | 5/2009 |
| JP | 2009-161613 | 7/2009 |
| WO | 2006/001387 | 1/2006 |
| WO | 2009-145323 | 12/2009 |
| WO | 2011/027865 | 3/2011 |

OTHER PUBLICATIONS

Cella et al., "Nitroxide-Catalyzed Oxidation of Alcohols Using m-Chloroperbenzoic Acid. A New Method", The Journal of Organic Chemistry, vol. 40, No. 12, 1975, pp. 1860-1862.
Anelli et al., "Fast and Selective Oxidation of Primary Alcohols to Aldehydes or to Carboxylic Acids and of Secondary Alcohols to Ketones Mediated by Oxoammonium Salts under Two-Phase Conditions", The Journal of Organic Chemistry, vol. 52, No. 12, 1987, pp. 2559-2562.
De Mico et al., "A Versatile and Highly Selective Hypervalent Iodine (III)/2,2,6,6-Tetramethyl-1-piperidinyloxyl-Mediated Oxidation of Alcohols to Caronyl Compounds", The Journal of Organic Chemistry, vol. 62, No. 20, 1997, pp. 6974-6977.
Semmelhack et al., "Oxidation of Alcohols to Aldehydes with Oxygen and Cupric Ion, Mediated by Nitrosonium Ion", Journal of the American Chemical Society, vol. 106, No. 11, 1984, pp. 3374-3376.
Liu et al., "Transition-Metal-Free: A Highly Efficient Catalytic Aerobic Alcohol Oxidation Process", Journal of the American Chemical Society, vol. 126, No. 13, 2004, pp. 4112-4113.
Shibuya et al., "2-Azaadamantane N-Oxyl (AZADO) and 1-Me-AZADO: Highly Efficient Organocatalysts for Oxidation of Alcohols", Journal of the American Chemical Society, vol. 128, No. 26, 2006, pp. 8412-8413.

(Continued)

*Primary Examiner* — Sikarl Witherspoon
(74) *Attorney, Agent, or Firm* — Greenblum & Bernstein, P.L.C.

(57) ABSTRACT

A method for oxidizing an alcohol, wherein oxidation is performed in the presence of a compound represented by the following formula (I) and a bulk oxidant, which enables efficient oxidation of secondary alcohols as well as primary alcohols, and can attain high reaction efficiency even when air is used as a bulk oxidant.

(I)

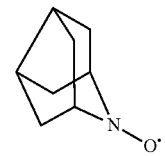

8 Claims, 1 Drawing Sheet

(56) References Cited

OTHER PUBLICATIONS

Shibuya et al., "An Expeditious Entry to 9-Azabicycleo[3.3.1]nonane N-Oxyl (ABNO): Another Highly Active Organocatalyst for Oxidation of Alcohols", The Journal of Organic Chemistry, vol. 74, No. 12, 2009, pp. 4619-4622.

Dupeyre et al., "Nitroglycerides—LXXVI Couplages a Longue Distance Dans Les Nitroxydes Azatricycliques. Etude Par RPE et RMN. Conformation Du Groupement Nitroxyde", Tetrahedron, vol. 34, No. 10, 1978, pp. 1501-1507.

Cao et al., "DEAD-(cat)ZnBr2 an efficient system for the oxidation of alcohols to carbonyl compounds", Tetrahedron Letters, vol. 50, 2009, pp. 1493-1494.

Yoneda et al., "A New Hydrogen-Abstracting Reaction with Diethyl Azodicarboxylate", Journal of the American Chemical Society, vol. 88, No. 10, 1966, pp. 2328-2329.

Dupeyre et al., "Nitroxydes LXXIII: Oxydation D'Amines Secondaires Et Tertiaires Par Le Permanganate De Potassium En Milieu Basique", Tetrahedron Letters, No. 22+23, 1975, pp. 1839-1840.

Demizu et al., "Efficient oxidation of alcohols electrochemically mediated by azabicyclo-N-oxyls", Tetrahedron Letters, vol. 49, No. 1, Jan. 2008, pp. 48-52.

Search report from International Application No. PCT/JP2011/062324, mail date is Jul. 5, 2011.

International Preliminary Report on Patentability and Written Opinion of the Searching Authority for International Application No. PCT/JP2011/062324, mail date is Jan. 31, 2013.

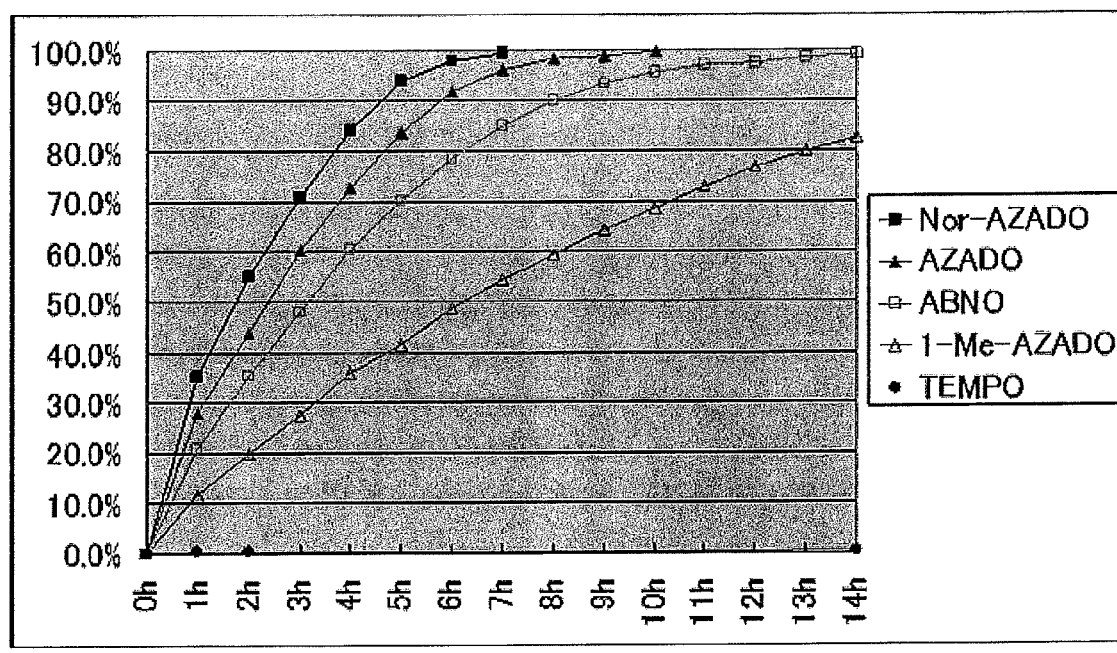

METHOD FOR OXIDIZING ALCOHOLS

TECHNICAL FIELD

The present invention relates to a method for oxidizing an alcohol utilizing an organic catalyst.

BACKGROUND ART

Oxidation reactions of alcohols constitute one class of important reactions as methods for chemical conversion of compounds, and are frequently used in syntheses of organic compounds with high added values such as medicaments and agricultural chemicals and the like. Therefore variety of methods have been developed so far. However, many of those methods use explosive reagents, highly toxic metals and the like, or place heavy load on the environment, such as production of huge amounts of waste matters. Employment of environment-friendly and safe synthetic methods has been desired especially in the field of industrial processes, and accordingly, several methods have been developed for oxidation reaction of alcohols from the aforementioned point of view.

For example, the oxidation reaction using 2,2,6,6-tetramethylpiperidine N-oxyl (henceforth also abbreviated as "TEMPO" in the specification) is a reaction in which TEMPO serves as an organic oxidation catalyst, and an oxoammonium salt generated from nitroxy radical derived from TEMPO acts as a chemical species having an oxidation activity. This oxidation reaction can achieve oxidation at a relatively low cost, and further, the reaction does not use highly toxic transition metals, and advances even under a mild condition such as at about 0° C. to room temperature. Therefore, this reaction has recently been focused as a highly environment-friendly oxidation reaction.

As for the oxidation reaction that uses TEMPO, since from the catalytic oxidation reaction utilizing m-chloroperbenzoic acid as a bulk oxidant was reported (Non-patent document 1), methods utilizing various bulk oxidants in combination have been developed. For example, there have been reported methods of using sodium hypochlorite, which has been most widely used in the present industrial processes because of inexpensiveness and less load on the environment, or diacetoxyiodobenzene, which accepts coexistence of a wide variety of functional groups, as a bulk oxidant (Non-patent documents 2 and 3). Methods of using more environment-friendly oxygen as a bulk oxidant have also been actively studied (Non-patent documents 4 and 5).

As mentioned above, the TEMPO oxidation has given a position as a potent oxidation method in the field of organic synthetic chemistry and industrial chemical processes. However, this oxidation often has a problem of low reactivity especially in oxidation of secondary alcohols due to insufficient reactivity for a bulky substrate. In order to solve this problem, there have been proposed 1-methyl-2-azaadamantane N-oxyl (henceforth also abbreviate as "1-Me-AZADO" in the specification), and 2-azaadamantane N-oxyl (henceforth also abbreviate as "AZADO" in the specification), which are nitroxyl radicals having the azaadamantane structure, as well as 9-azabicyclo[3.3.1]nonane N-oxyl (henceforth also abbreviate as "ABNO" in the specification), which is a bicyclo type nitroxyl radical (Non-patent documents 6 and 7 and Patent documents 1 and 2). It has been confirmed that 1-Me-AZADO, AZADO, and ABNO have a catalytic activity far higher than that of TEMPO, and it has been elucidated that they have high catalytic activity not only for oxidation of primary alcohols, but also for oxidation of secondary alcohols, which hardly advances with TEMPO.

However, the synthesis of 1-Me-AZADO has a problem that it requires seven steps from a commercially available compound. Although ABNO can be synthesized by three steps from a commercially available compound, it has a lower catalytic activity compared with those of AZADO and 1-Me-AZADO when an amount added is small, and thus it has problems from environment compatibility and economical viewpoints. When air is used as a bulk oxidant, which has superior environment compatibility, each of 1-Me-AZADO, AZADO, and ABNO achieves a slow reaction rate at a catalyst amount of about 1 mol %, and thus they have a problem from a viewpoint of reaction efficiency. Although the compound represented by the following formula (I) (Nor-AZADO) is disclosed in Non-patent document 8, no use of the compound as an oxidation catalyst is suggested or taught.

PRIOR ART REFERENCES

Patent Documents

Patent document 1: Japanese Patent Unexamined Publication (KOKAI) No. 2008-212853
Patent document 2: International Patent Publication WO2006/001387

Non-Patent Documents

Non-patent document 1: The Journal of Organic Chemistry, Vol. 40, No. 12, pp. 1860-1862, 1975
Non-patent document 2: The Journal of Organic Chemistry, Vol. 52, No. 12, pp. 2559-2562, 1987
Non-patent document 3: The Journal of Organic Chemistry, Vol. 62, No. 20, pp. 6974-6977, 1997
Non-patent document 4: Journal of the American Chemical Society, Vol. 106, No. 11, pp. 3374-3376, 1984
Non-patent document 5: Journal of the American Chemical Society, Vol. 126, No. 13, pp. 4112-4113, 2004
Non-patent document 6: Journal of the American Chemical Society, Vol. 128, No. 26, pp. 8412-8413, 2006
Non-patent document 7: The Journal of Organic Chemistry, Vol. 74, No. 12, pp. 4619-4622, 2009
Non-patent document 8: Tetrahedron, Vol. 34, No. 10, pp. 1501-1507, 1978
Non-patent document 9: Tetrahedron Letters, Vol. 50, pp. 1493-1494, 2009
Non-patent document 10: Journal of the American Chemical Society, Vol. 88, No. 10, pp. 2328-2329, 1966

SUMMARY OF THE INVENTION

Object to be Achieved by the Invention

An object of the present invention is to provide a method for efficiently oxidizing an alcohol by using an organic catalyst. More specifically, the object of the present invention is to provide such an oxidation method as mentioned above that enables efficient oxidation of secondary alcohols as well as primary alcohols, and can attain high reaction efficiency even when air is used as a bulk oxidant.

Means for Achieving the Object

The inventors of the present invention conducted various researches to achieve the aforementioned object, and as a result, they found that when 9-norazaadamantane N-oxyl (henceforth also abbreviated as "Nor-AZADO" in the specification) formed by incorporating the nitroxyl radical into the norazaadamantane structure was used as an organic oxidation catalyst, oxidation efficiently advanced even for secondary alcohols and a higher catalyst turnover compared with those of 1-Me-AZADO, AZADO, and ABNO was successfully obtained, and further, the compound successfully gave higher catalytic activity compared with 1-Me-AZADO, AZADO, and ABNO even in a reaction using air as a bulk oxidant to complete the reaction in a shorter time. The present invention was accomplished on the basis of the aforementioned findings.

The present invention thus provides a method for oxidizing an alcohol, wherein oxidation is performed in the presence of a compound represented by the following formula (I):

[Formula 1]

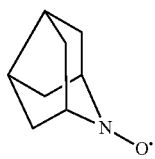

(I)

and a bulk oxidant.

According to preferred embodiments of the aforementioned invention, there are provided the aforementioned method, wherein the alcohol is a primary alcohol or a secondary alcohol; the aforementioned method, wherein an amount of the compound represented by the formula (I) is a catalytic amount; the aforementioned method, wherein the amount of the compound represented by the formula (I) is in the range of 0.0001 to 100 mol % based on the alcohol; the aforementioned method, wherein the amount of the compound represented by the formula (I) is in the range of 0.001 to 5 mol % based on the alcohol; the aforementioned method, wherein the bulk oxidant is a peracid, hydrogen peroxide, a hypohalogen acid or a salt thereof, a perhalogen acid or a salt thereof, a persulfuric acid salt, a halogenating agent such as a halide and N-bromosuccinimide, a trihalogenated isocyanuric acid, a diacetoxyiodoallene, a dialkyl azodicarboxylate, oxygen, air, or a mixture there; the aforementioned method, wherein the bulk oxidant is air; and the aforementioned method, wherein a hydroxylamine compound and/or an oxoammonium salt of 9-norazaadamantane is used together with or instead of the compound represented by the formula (I).

Effect of the Invention

According to the method of the present invention, the method is characterized in that a bulky alcohol which is hardly oxidized with the conventional TEMPO, especially a secondary alcohol compound, can be efficiently oxidized, and the reaction advances even at room temperature and ordinary pressure without using, for example, any transition metal. Further, according to the method of the present invention, the reaction advances with a smaller amount of the catalyst compared with the methods utilizing 1-Me-AZADO, AZADO, or ABNO as an organic catalyst, and the catalyst can be obtained at a lower cost. Therefore, the method is remarkably advantageous from an economical point of view in industrial processes compared with the methods of using AZADO or the like. Accordingly, the method of the present invention has characteristic feature that the method is more economical compared with the conventional oxidization methods for alcohols, and it places less load on the environment. Further, when air is used as a bulk oxidant, the reaction advances within a shorter time as compared with the oxidization methods utilizing 1-Me-AZADO, AZADO, or ABNO, and therefore load on the environment can be reduced.

BRIEF DESCRIPTION OF THE DRAWING

FIG. 1 This FIGURE is a graph showing change of conversion ratio over time in oxidization of menthol, which is a bulky secondary alcohol, using air as a bulk oxidant

MODES FOR CARRYING OUT THE INVENTION

The method of the present invention is for oxidizing an alcohol, and it is characterized by performing oxidization in the presence of a compound represented by the aforementioned formula (I) (henceforth also abbreviated as "Compound (I)" in the specification) and a bulk oxidant. As the alcohol used as the object to be oxidized, any of a primary alcohol or a secondary alcohol may be used. High oxidation efficiency can be achieved by the method of the present invention as compared with the conventional methods using TEMPO even when a secondary alcohol is used as the substrate compound, and accordingly, a secondary alcohol can be used as a preferred substrate compound. By applying the method of the present invention, a primary alcohol or a secondary alcohol is converted into a corresponding aldehyde or ketone compound.

A compound represented by the formula (I) can be easily and inexpensively synthesized through four steps from commercially available glutaraldehyde, acetonedicarboxylic acid, and benzylamine, as the method for synthesis thereof is shown in Non-patent document 8. Specific preparation methods are described in the examples mentioned in the specification.

According to the method of the present invention, the primary alcohol is, for example, a compound represented by the following general formula (II), and the secondary alcohol is, for example, a compound represented by the following general formula (III). In the general formulas (II) and (III), the substituents X and Y are not particularly limited, so long as the substituent does not adversely affect the reaction. Examples of X and Y include, for example, a linear or branched alkyl group which may be substituted, a cyclic alkyl group which may be substituted, an aromatic hydrocarbon group which may be substituted, and an aromatic heterocyclic group which may be substituted. X and Y may be the same or different.

[Formula 2]

(II)

(III)

Examples of the linear or branched alkyl group include an alkyl group having about 1 to 16 carbon atoms. As the alkyl group, an alkyl group having about 1 to 8 carbon atoms can be preferably used. Examples of the alkyl group include, for example, methyl group, ethyl group, n-propyl group, isopropyl group, n-butyl group, isobutyl group, s-butyl group, tert-butyl group, n-pentyl group, isopentyl group, 2-methylbutyl group, neopentyl group, 1-ethylpropyl group, n-hexyl group, isohexyl group, 4-methylpentyl group, 3-methylpentyl group, 2-methylpentyl group, 1-methylpentyl group, 3,3-dimethylbutyl group, 2,2-dimethylbutyl group, 1,1-dimethylbutyl group, 1,2-dimethylbutyl group, 1,3-dimethylbutyl group, 2,3-dimethylbutyl group, 2-ethylbutyl group, heptyl group, 1-methylhexyl group, 2-methylhexyl group, 3-methylhexyl group, 4-methylhexyl group, 5-methylhexyl group, 1-propylbutyl group, 4,4-dimethylpentyl group, octyl group, 1-methylheptyl group, 2-methylheptyl group, 3-methylheptyl group, 4-methylheptyl group, 5-methylheptyl group, 6-methylheptyl group, 1-propylpentyl group, 2-ethylhexyl group, 5,5-dimethylhexyl group, and the like.

Examples of the cyclic alkyl group include a cycloalkyl group having about 3 to 7 carbon atoms, for example, cyclopropyl group, cyclobutyl group, cyclopentyl group, cyclohexyl group, cycloheptyl group, and the like.

The aromatic ring constituting the aromatic hydrocarbon group may be a monocyclic aromatic hydrocarbon ring or a condensed polycyclic aromatic hydrocarbon ring. Examples of the aromatic hydrocarbon group include, for example, an aryl group having about 6 to 14 carbon atoms, such as phenyl group, naphthyl group, anthryl group, azulenyl group, phenanthryl group, and acenaphthylenyl group.

Examples of the heterocyclic ring constituting the aromatic heterocyclic group include, for example, a 5- or 6-membered monocyclic heterocyclic ring, and a condensed heterocyclic ring containing a 6-membered ring and a 5-membered ring, or a 6-membered ring and a 6-membered ring, but are not limited to these examples. Examples of the ring-constituting heteroatom constituting the heterocyclic ring include, for example, 1 to 3 atoms selected from oxygen atom, sulfur atom, and nitrogen atom, but are not limited to these examples. Although the heterocyclic ring is preferably an aromatic ring, it may be a saturated or partially saturated ring. When the heterocyclic ring is a saturated or partially saturated ring, the heteroatom moiety thereof may often be preferably protected with an appropriate protective group, or may be not protected.

Examples of the aromatic heterocyclic group include, for example, a monocyclic aromatic heterocyclic group, such as furyl group, thienyl group, pyrrolyl group, oxazolyl group, isoxazolyl group, thiazolyl group, isothiazolyl group, imidazolyl group, pyrazolyl group, 1,2,3-oxadiazolyl group, 1,2,4-oxadiazolyl group, 1,3,4-oxadiazolyl group, furazanyl group, 1,2,3-thiadiazolyl group, 1,2,4-thiadiazolyl group, 1,3,4-thiadiazolyl group, 1,2,3-triazolyl group, 1,2,4-triazolyl group, tetrazolyl group, pyridyl group, pyridazinyl group, pyrimidinyl group, pyrazinyl group, and triazinyl group, and a 8- to 12-membered condensed polycyclic aromatic heterocyclic group, such as benzofuranyl group, isobenzofuranyl group, benzo[b]thienyl group, indolyl group, isoindolyl group, 1H-indazolyl group, benzindazolyl group, benzoxazolyl group, 1,2-benzoisoxazolyl group, benzothiazolyl group, benzopyranyl group, 1,2-benzoisothiazolyl group, 1H-benzotriazolyl group, quinolyl group, isoquinolyl group, cinnolinyl group, quinazolinyl group, quinoxalinyl group, phthalazinyl group, naphthyridinyl group, purinyl group, pteridinyl group, carbazolyl group, a-carbolinyl group, 8-carbolinyl group, γ-carbolinyl group, acridinyl group, phenoxazinyl group, phenothiazinyl group, phenadinyl group, phenoxathiinyl group, thianthrenyl group, phenanthridinyl group, phenanthrolinyl group, indolidinyl group, pyrrolo[1,2-b]pyridazinyl group, pyrazolo[1,5-a]pyridyl group, imidazo[1,2-a]pyridyl group, imidazo[1,5-a]pyridyl group, imidazo[1,2-b]pyridazinyl group, imidazo[1,2-a]pyrimidinyl group, 1,2,4-triazolo[4,3-a]pyridyl group, and 1,2,4-triazolo[4,3-b]pyridazinyl group. These aromatic heterocyclic groups may be saturated or partially saturated.

In the specification, when "which may be substituted" is referred to as for a certain group, the phrase means that the group may have one or two or more arbitrary substituents at arbitrary positions on the group, and when the group has two or more substituents, they may be the same or different. Types of the substituents are not particularly limited so long as they do not adversely affect the reaction.

Examples of the substituent that can exist on the linear or branched alkyl group, the cyclic alkyl group, the aromatic hydrocarbon group, or the aromatic heterocyclic group include, for example, an alkyl group having about 1 to 6 carbon atoms such as methyl group, ethyl group, and propyl group, an alkoxy group having about 1 to 6 carbon atoms such as methoxy group, ethoxy group, and propoxy group, a halogen atom such as fluorine atom, chlorine atom, bromine atom, and iodine atom, an alkenyl group having about 2 to 6 carbon atoms such as vinyl group and allyl group, an alkynyl group having about 2 to 6 carbon atoms such as ethynyl group and propargyl group, hydroxyl group, an amino group which may be substituted, a sulfonyl group which may be substituted, a sulfonamido group which may be substituted, cyano group, nitro group, nitroso group, an amidino group which may be substituted, carboxy group, an alkoxycarbonyl group having about 2 to 7 carbon atoms, a carbamoyl group which may be substituted, an aromatic group, an aromatic heterocyclic group, an acyl group (for example, an alkylcarbonyl group which may be substituted, or an arylcarbonyl group which may be substituted), and the like, but are not limited to these examples. These substituents may be appropriately protected. Although type of protective group is not particularly limited, protective groups suitable for hydroxyl group, amino group, and the like can be appropriately chosen by referring to a publication, for example, Green et al., Protective Groups in Organic Synthesis, 3rd Edition, 1999, John Wiley & Sons, Inc., and the like, and they can be removed with an appropriate means from an aldehyde or ketone compound as the product of the oxidation of alcohol.

In the method of the present invention, the "bulk oxidant (also called "reoxidation agent" or "cooxidizer")" is a supply source of oxidation ability for the compound represented by the formula (I) as an organic catalyst. The bulk oxidant is not particularly limited, so long that the agent can oxidize hydroxylamine into a nitroxyl radical or an oxoammonium salt, or can oxidize a nitroxyl radical into an oxoammonium salt. The agent can generally be chosen appropriately from, for example, those used as a bulk oxidant in the oxidation reaction using TEMPO.

As the bulk oxidant, there can be used, for example, a peracid, hydrogen peroxide, a hypohalogen acid or a salt thereof, a perhalogen acid or a salt thereof, a persulfuric acid salt, a halogenating agent such as a halide and N-bromosuccinimide, a trihalogenated isocyanuric acid, a diacetoxyiodoallene, oxygen, air, or a mixture thereof, but the oxidant is not limited to these examples. There can be preferably used, for example, peracetic acid, m-chloroperbenzoic acid, hydrogen peroxide, sodium hypochlorite, lithium hypochlorite, potassium hypochlorite, calcium hypochlorite, sodium hypobromite, lithium hypobromite, potassium hypobromite, calcium hypobromite, sodium hydrogenpersulfate, sodium periodate, periodic acid, trichloroisocyanuric acid, tribromoisocyanuric acid, N-bromosuccinimide, N-chlorosuccinimide, chlorine, bromine, iodine, diacetoxyiodobenzene, oxygen, or air. The method of the present invention can attain high oxidation efficiency even when air is used as the bulk oxidant, and accordingly, the method using air as the bulk oxidant is a preferred embodiment of the present invention.

As the bulk oxidant used for the oxidization method of the present invention, a dialkyl azodicarboxylate may also be employed. The dialkyl azodicarboxylate is not particularly limited, so long that a usually used dialkyl azodicarboxylate is chosen, and such an ester comprising alkyl groups having 1 to 6 carbon atoms can be preferably used. As the dialkyl azodicarboxylate, diisopropyl azodicarboxylate (henceforth also abbreviated as "DIAD" in the specification) is preferred, and diethyl azodicarboxylate can also be used.

The oxidation reaction according to the method of the present invention may be performed in the presence or absence of a solvent. When a solvent is used, type of the solvent is not particularly limited, so far that the solvent does not inhibit the reaction. Examples of the solvent include, for example, an aliphatic hydrocarbon such as hexane, heptane, and petroleum ether, an aromatic hydrocarbon such as benzene, toluene, and xylene, a nitrile such as acetonitrile, propionitrile, and benzonitrile, a halogenated hydrocarbon such as dichloromethane, chloroform, 1,2-dichloroethane, and carbon tetrachloride, an ether such as diethyl ether, diisopropyl ether, tetrahydrofuran, dioxane, dimethoxyethane, and diethylene glycol dimethyl ether, an amide such as formamide, dimethylformamide, dimethylacetamide, and hexamethylphosphoric triamide, a sulfoxide such as dimethyl sulfoxide, an ester such as ethyl formate, ethyl acetate, propyl acetate, butyl acetate, and diethyl carbonate, a carboxylic acid such as acetic acid, formic acid, and propionic acid, sulfolane, water, and the like, and these may also be used as a mixture. An aliphatic hydrocarbon, an aromatic hydrocarbon, a nitrile, a halogenated hydrocarbon, an ester, a carboxylic acid, water, and a mixture thereof can be preferably used, and dichloromethane, acetonitrile, acetic acid, toluene, ethyl acetate, isopropyl acetate, water, and a mixture thereof can be more preferably used. Dichloromethane, a mixed solution of dichloromethane and water, a mixed solution of toluene and water, a mixed solution of ethyl acetate and water, acetonitrile, and acetic acid can be most preferably used.

The reaction mixture may optionally contain a buffering agent such as an inorganic salt or an organic salt. Examples of the buffering agent include, for example, an alkali metal or alkaline earth metal carbonate, an alkali metal or alkaline earth metal bicarbonate, an alkali metal or an alkaline earth metal hydroxide, an alkali metal or alkaline earth metal phosphate, an alkali metal or alkaline earth metal acetate, and the like, and preferred examples include sodium hydrogencarbonate, sodium carbonate, sodium acetate, a phosphoric acid salt, and the like.

The reaction mixture may also optionally contain an additive for promoting the reaction. Examples of such an additive include, for example, a quaternary ammonium salt, an alkali metal halide, and the like in the case where sodium hypochlorite as the bulk oxidant is used, and preferred examples include tetrabutylammonium chloride, tetrabutylammonium bromide, sodium bromide, potassium bromide, a mixture thereof and the like. In the case where oxygen as the bulk oxidant is used, the additive can be chosen from the additives generally used for the air oxidation reaction using TEMPO. For example, as the additive, there can be used a nitrous acid salt, an inorganic acid, an organic acid, bromine, a salt of a transition metal such as copper, iron, and ruthenium, and a mixture of sodium nitrite and acetic acid, a mixture of sodium nitrite and bromine, a mixture of sodium nitrite and ferric chloride, and copper chloride can be preferably used as the additive.

When the reaction is performed by using a dialkyl azodicarboxylate as the bulk oxidant, it is generally required to perform the reaction in the presence of a weakly acidic substance. The weakly acidic substance may be an organic acid or an inorganic acid. It is convenient to add an aliphatic carboxylic acid. The aliphatic carboxylic acid may be an aliphatic carboxylic acid having about 2 to 7 carbon atoms, and examples include acetic acid, propionic acid, butyric acid, valeric acid, and the like. Among them, acetic acid can be preferably used. Examples also include benzoic acid, which is an aromatic carboxylic acid. The weak acid can be used usually in an amount in the range of 0.1 to 5 equivalents, preferably about 1 to 2 equivalents, based on the alcohol.

Although the amount of Compound (I) based on the alcohol is not particularly limited, the amount may be, based on the alcohol, usually 0.0001 to 100 mol % (it means that Compound (I) is used in an amount of 0.0001 to 100% of the starting material alcohol in terms of molar number), preferably about 0.001 to 5 mol %. When air is used as the bulk oxidant, it is preferably used in an amount of about 0.1 to 5 mol %.

Although the reaction temperature may vary depending on conditions such as type of the alcohol, type and amount of the bulk oxidant, and presence or absence of the additive, the temperature is usually in the range of −80 to 120° C., preferably in the range of 0 to 40° C. After completion of the reaction, the reaction system can be subjected to a usual post treatment, and then the objective oxidation product can be isolated by an ordinary isolation operation such as extraction, recrystallization, and column chromatography. Two or more kinds of isolation operations may be used in combination.

Although it is not intended to be bound by any specific theory, it is considered that the oxidation reaction performed by using Compound (I) according to the present invention advances according to the reaction mechanism generally supposed for the oxidation reaction performed by using TEMPO as the catalyst (namely, the reaction mechanism in which TEMPO serves as an organic oxidation catalyst, and an oxoammonium salt generated from a nitroxy radical derived from TEMPO acts as a chemical species having oxidation activity). Therefore, it is apparent to those skilled in the art that a hydroxylamine compound and/or an oxoammonium salt of 9-norazaadamantane can be used together with Compound (I) of the present invention, or instead of Compound (I) as an equivalent, and it should be understood that such an embodiment falls within the scope of the present invention.

EXAMPLES

Hereafter, the present invention will be still more specifically explained with reference to examples. However, the scope of the present invention is not limited by the following examples. In the examples, Bn represents benzyl group, Ts represents p-toluenesulfonyl group, Ph represents phenyl group, Cbz represents benzyloxycarbonyl group, TBS represents tert-butyldimethylsilyl group, and Me represents methyl group.

Example 1

(a) Synthesis of 9-benzyl-9-azabicyclo[3.3.1]nonan-3-one

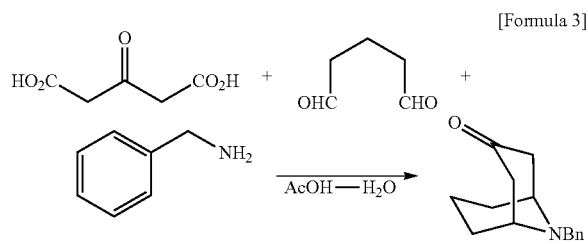

A solution of acetonedicarboxylic acid (16.1 g, 109.9 mmol) in a mixture of acetic acid (46 ml) and water (92 ml) was successively added dropwise with 50% aqueous glutaraldehyde (26.5 ml, 146.5 mmol), and benzylamine (10 ml, 91.6 mmol) at room temperature, and then the mixture was stirred at the same temperature for 9 hours. The reaction mixture was added with dichloromethane (50 ml), and made basic by addition of 5 M aqueous sodium hydroxide (180 ml), and the mixture was extracted with dichloromethane. The organic layer was washed with saturated brine, and then dried over sodium sulfate. The organic layer was concentrated under reduced pressure, and then the residue was purified by silica gel column chromatography to obtain crude crystals (17.2 g). The crude crystals were added with ethyl acetate (5 ml) and hexane (50 ml), and the slurry was stirred for 24 hours. The crystals were collected by filtration, washed with a mixed solution of ethyl acetate and hexane (10:1), and then dried under reduced pressure to obtain the objective compound (12.7 g, 60.6%).

$^1$H-NMR (CDCl$_3$, 400 MHz): δ 7.41-7.24 (m, 5H), 3.91 (s, 2H), 3.31 (brs, 2H), 2.73 (dd, 2H, J=16.7, 6.5 Hz), 2.25 (d, 2H, J=16.7 Hz), 1.98-1.90 (m, 2H), 1.56-1.46 (m, 4H).

$^{13}$C-NMR (CDCl$_3$, 100 MHz): δ 211.5, 139.2, 128.4, 128.3, 127.1, 57.1, 53.5, 42.9, 29.3, 16.5.

IR (CHCl$_3$, cm$^{-1}$): 1704.

EI-MS m/z: 229 (M$^+$).

HRMS (EI): calcd. for C$_{15}$H$_{19}$O$_1$N$_1$ 229.1467 (M$^+$), Found: 229.1460.

(b) Synthesis of N-(9-benzyl-9-aza-bicyclo[3.3.1]non-3-ylidene)-N'-p-toluenesulfonylhydrazine

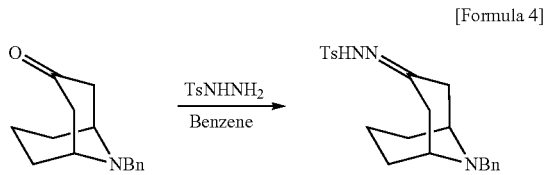

A solution of 9-benzyl-9-azabicyclo[3.3.1]nonan-3-one (13.7 g, 59.7 mmol) and tosylhydrazone (12.2 g, 65.7 mmol) in benzene (199 ml) was dehydrated by refluxing for 24 hours under ordinary pressure. The reaction mixture was cooled to room temperature, and then concentrated under reduced pressure, the residue was added with a mixed solution of methanol and isopropanol (1:1, 164 ml), and the resulting slurry was stirred for 1 hour under ice cooling. The crystals were collected by filtration, washed with a mixed solution of methanol and isopropanol (1:1), and then dried under reduced pressure to obtain the objective compound (15.7 g, 66.3%).

$^1$H-NMR (CDCl$_3$, 400 MHz): δ 7.85 (d, 2H, J=8.2 Hz), 7.36-7.22 (m, 7H), 3.49 (d, 1H, J=5.1), 3.10-3.06 (m, 2H), 2.66 (dd, 1H, J=6.5, 16.2 Hz), 2.43 (s, 3H), 2.33 (brs, 1H), 2.31 (d, 2H, J=16.2 Hz), 1.90-1.89 (m, 2H), 1.48-1.34 (m, 4H).

$^{13}$C-NMR (CDCl$_3$, 100 MHz): δ 161.8, 143.9, 139.2, 135.7, 129.5, 128.3, 128.3, 128.0, 127.0, 56.8, 52.0, 51.4, 34.9, 29.5, 28.7, 28.2, 21.6, 16.8.

IR (CHCl$_3$, cm$^{-1}$): 3217, 1598.

EI-MS m/z: 397 (M$^+$).

HRMS (EI): calcd. for C$_{22}$H$_{27}$O$_2$N$_3$S 397.1824 (M$^+$), Found: 397.1815.

(c) Synthesis of 9-benzyl-9-norazaadamantane

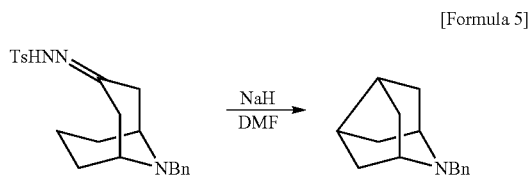

A solution of N-(9-benzyl-9-aza-bicyclo[3.3.1]non-3-ylidene)-N'-p-toluenesulfonylhydrazine (10.0 g, 25.2 mmol) in dimethylformamide (252 ml) was added with sodium hydride (60% in mineral oil, 3.02 g, 75.5 mmol) at room temperature, and the mixture was refluxed by heating for 3 hours. The reaction mixture was cooled to room temperature, and then added with 10% brine (100 ml), and the mixture was extracted with diethyl ether. The organic layer was dried over sodium sulfate, and then concentrated under reduced pressure. The residue was purified by silica gel column chromatography to obtain the objective substance (3.56 g, 66.4%).

$^1$H NMR (CDCl$_3$, 400 MHz): δ 7.36-7.19 (m, 5H), 3.71 (s, 2H), 3.15 (brs, 2H), 2.55 (m, 2H), 1.84 (d, 2H, J=10.1 Hz), 1.47 (m, 4H).

$^{13}$C-NMR (CDCl$_3$, 100 MHz): δ 140.4, 128.7, 128.1, 126.5, 60.7, 58.0, 40.1, 36.2.

IR (CHCl$_3$, cm$^{-1}$): 1493, 1453, 1357, 1317.

EI-MS m/z: 213 (M$^+$).

HRMS (EI): calcd. for C$_{15}$H$_{19}$N$_1$ 223.1517 (M$^+$), Found: 223.1512.

(d) Synthesis of compound of the formula (I) (Nor-AZADO, 9-norazaadamantane N-oxyl)

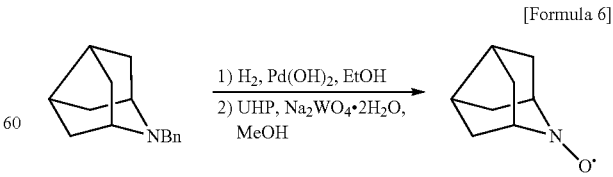

A solution of 9-benzyl-9-norazaadamantane (2.07 g, 9.69 mmol) in ethanol (48.5 ml) was added with palladium hydroxide (50% wet, 0.62 g) at room temperature under a nitrogen atmosphere. The reaction mixture was stirred at room temperature for 25 hours under a hydrogen atmosphere. The reaction mixture was filtered through Celite, and washed with dichloromethane (50 ml). The filtrate and the washing solution were dried over potassium carbonate, and then the solvent was evaporated to dryness under reduced pressure to obtain 9-norazaadamantane (1.07 g). The resulting 9-norazaadamantane was dissolved in methanol (16.5 ml), then the solution was added with sodium tungstate dihydrate, and the mixture was stirred at room temperature for 30 minutes. The reaction mixture was added with a urea hydrogen peroxide adduct, and the mixture was stirred at room temperature for 3 hours. The reaction mixture was concentrated under reduced pressure, and then added with saturated aqueous sodium hydrogencarbonate (15 ml), and the mixture was extracted with chloroform. The organic layer was dried over sodium sulfate, and then concentrated under reduced pressure, and the residue was purified by silica gel column chromatography to obtain the objective compound (0.634 mg, 49.7%).

IR (CHCl$_3$, cm$^{-1}$): 1454.1, 1336.4, 1277.6.

EI-MS m/z: 138 (M$^+$).

HRMS (EI): calcd. for C$_8$H$_{12}$ON 138.0919 (M$^+$), Found: 138.0915.

Anal: Calcd. for C$_8$H$_{12}$ON: C, 69.53; H, 8.75; N, 10.14. Found: C, 69.34; H, 8.62; N, 10.06.

Example 2

Oxidation reactions of alcohols were performed by using sodium hypochlorite as the bulk oxidant. Catalytic activities of Nor-AZADO as well as TEMPO, 1-Me-AZADO, AZADO, and ABNO for comparison were compared. The results are shown in Table 1.

In the oxidation of 4-phenylbutanol (entry 1), which is a primary alcohol, when the catalyst amount was 1 mol %, all the catalyst compounds gave the objective substance in a high yield, but when the catalyst amount was reduced, marked differences was observed in the catalytic activity. Specifically, in the case of using TEMPO, when the catalyst amount was reduced to 0.01 mol %, marked decrease of the yield was observed, and in the case of ABNO, when the catalyst amount was reduced to 0.003 mol %, the yield decreased to about 60%. In contrast, Nor-AZADO gave the objective substance in a high yield even when the catalyst amount was reduced to 0.003 mol %.

In the oxidation of 4-phenylbutan-2-ol (entry 2), which is a secondary alcohol, higher catalytic activity of Nor-AZADO was observed compared with 1-Me-AZADO and AZADO. Specifically, when the catalyst amount was reduced to 0.003 mol %, marked decrease of the yield was observed with 1-Me-AZADO, AZADO, and ABNO, but Nor-AZADO gave the objective substance at a yield higher than 90%. Further, in the oxidation of L-menthol (entry 3), which is a further bulkier secondary alcohol, TEMPO gave almost no catalytic activity even when the catalyst amount was 1 mol %, whilst high catalytic activity of Nor-AZADO was observed even at a catalyst amount of 0.003 mol %.

On the basis of the aforementioned results, it is clearly understood that Nor-AZADO is effective for oxidation of secondary alcohols, which is hardly conductible by using TEMPO as well as 1-Me-AZADO, AZADO, and ABNO, and can produce the objective substances in a high yield even when the catalyst amount is reduced, and accordingly, the compound has higher catalytic activity compared with 1-Me-AZADO, AZADO, and ABNO.

TABLE 1 alcohol $\xrightarrow[\text{CH}_2\text{Cl}_2\text{-sat. NaHCO}_3\text{aq. (1:1, 0.2M)}, 0°C.]{\substack{\text{nitroxy radicals}\\\text{NaOCl (1.5 eq.)}\\\text{KBr (10 mol \%), TBAB (5 mol \%)}}}$ ketone or aldehyde

| entry | substrates | products | catalyst lording ammount (mol %) | time | TEMPO | 1-Me-AZADO | AZADO | ABNO | Nor-AZADO |
|---|---|---|---|---|---|---|---|---|---|
| 1 | 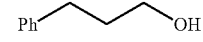 |  | 1 | 20 min | 89% | 91% | 91% | 91% | 92% |
|  |  |  | 0.01 | 20 min | 19% | 89% | 88% | 83% | 89% |
|  |  |  | 0.003 | 30 min | n.d.*[1] | 79% | 82% | 59% | 82% |
| 2 |  |  | 1 | 20 min | 97% | 99% | 99% | 100% | 99% |
|  |  |  | 0.01 | 30 min | 20% | 97% | 99% | 94% | 99% |
|  |  |  | 0.003 | 40 min | n.d.*[1] | 67% | 74% | 24% | 92% |
| 3 |  |  | 1 | 20 min | 5% | 95% | 99% | 94% | 99% |
|  |  |  | 0.01 | 30 min | n.d.*[1] | 61% | 98% | 95% | 98% |
|  |  |  | 0.003 | 40 min | n.d.*[1] | 25% | 87% | 8% | 92% |

*[1]not determined.

Example 3

Catalytic activities for oxidation of alcohols using air as the bulk oxidant were compared. The results are shown in Table 2.

TABLE 2 alcohol → ketone
nitroxy radicals (1 mol %)
NaNO$_2$ (20 mol %), AcOH (2 eq.)
MeCN (1M), Air (balloon), r.t.

| entry | substrates | products | Conversion* (time) | | | | |
|---|---|---|---|---|---|---|---|
| | | | TEMPO | 1-Me-AZADO | AZADO | ABNO | Nor-AZADO |
| 1 | Ph-CH$_2$CH$_2$CH(OH)CH$_3$ | Ph-CH$_2$CH$_2$C(O)CH$_3$ | 5% (13 h) | 99% (9 h) | 100% (7 h) | 99% (12 h) | 100% (6 h) |
| 2 | menthol | menthone | 0% (14 h) | 83% (14 h) | 100% (10 h) | 99% (14 h) | 100% (7 h) |
| 3 | isopinocampheol | isopinocamphone | 0% (14 h) | 99% (10 h) | 100% (8 h) | 99% (10 h) | 100% (6 h) |

*GC

It was revealed that, also under the air oxidation condition, Nor-AZADO had higher catalytic activity compared with the conventional catalysts. In the entries 1, 2, and 3, the reaction advanced at a high conversion rate with Nor-AZADO, 1-Me-AZADO, AZADO, and ABNO, whereas no reaction advanced or almost no reaction advanced with TEMPO. As a result of comparison of the reaction times, it was revealed that when Nor-AZADO was used, the reaction was completed in the shortest times for all the substrates, and thus Nor-AZADO had the highest activity among all the catalysts including the conventional catalysts. Change of the conversion rates over time in the air oxidation reaction of menthol as the substrate (entry 2) is shown in FIG. 1. On the basis of the results shown above, it is clear that when air is used as the 'bulk oxidant, Nor-AZADO functions as a more efficient catalyst compared with the conventional catalysts.

Example 4

Function of Nor-AZADO as oxidation catalyst was investigated for various alcohols. The results are shown in Table 3. The reactions advanced for various primary and secondary alcohols, and gave the objective aldehydes or ketones in high yields. The objective substances were obtained even from sterically bulky alcohols having a complicated structure, and therefore it is clear that Nor-AZADO is a superior oxidation catalyst.

TABLE 3 alcohol → ketone or aldehyde
method A: Nor-AZADO (1 mol %), NaNO$_2$ (20 mol %), AcOH (2 eq.) Air (balloon), MeCN (1M), r.t.
method B: Nor-AZADO (1 mol %), NaNO$_2$ (20 mol %) Air (balloon), AcOH (0.3M), r.t.

| entry | substrate | method | product | yield (time) |
|---|---|---|---|---|
| 1 | Ph-CH$_2$CH$_2$CH(OH)CH$_3$ | A | Ph-CH$_2$CH$_2$C(O)CH$_3$ | 98% (4 h) |
| 2 | menthol | A | menthone | 96% (6 h) |

TABLE 3-continued alcohol $\xrightarrow[\text{method B: Nor-AZADO (1 mol \%),}]{\text{method A: Nor-AZADO (1 mol \%),}}$ ketone or aldehyde
$\text{NaNO}_2$ (20 mol %), AcOH (2 eq.)
Air (balloon), MeCN (1M), r.t.
$\text{NaNO}_2$ (20 mol %)
Air (balloon), AcOH (0.3M), r.t.

| entry | substrate | method | product | yield (time) |
|---|---|---|---|---|
| 3 | (norbornanol derivative with OH) | A | (norbornanone derivative) | 92% (8 h) |
| 4 | Ph–CH(OH)–C(CH₃)₃ | A | Ph–C(O)–C(CH₃)₃ | 95% (7 h) |
| 5 | (CH₃)₃C–CH(OH)–(CH₂)₄CH₃ | A | (CH₃)₃C–C(O)–(CH₂)₄CH₃ | 87% (12 h) |
| 6 | trans-2-phenylcyclohexanol | A | 2-phenylcyclohexanone | 99% (4 h) |
| 7 | (diacetone-protected sugar with OH) | A | (diacetone-protected sugar ketone) | 90% (5 h) |
| 8 | 2-adamantanol | B | 2-adamantanone | 92% (22 h) |
| 9 | trans-4-(Cbz-amino)cyclohexanol | B | 4-(Cbz-amino)cyclohexanone | 73% (24 h) |
| 10 | 5'-TBS, 2'-OTBS adenosine (3'-OH) | B | 5'-TBS, 2'-OTBS-3'-keto adenosine | 80% (6 h) |
| 11 | 1-(pyridin-2-yl)ethanol | A | 2-acetylpyridine | 81% (3 h) |

TABLE 3-continued

| | alcohol | method A: Nor-AZADO (1 mol %), NaNO$_2$ (20 mol %), AcOH (2 eq.) Air (balloon), MeCN (1M), r.t. ⟶ method B: Nor-AZADO (1 mol %), NaNO$_2$ (20 mol %) Air (balloon), AcOH (0.3M), r.t. | ketone or aldehyde | |
|---|---|---|---|---|
| entry | substrate | method | product | yield (time) |
| 12 | Ph〜〜〜OH | A | Ph〜〜CHO | 89% (3 h) |
| 13 | 4-MeO-C$_6$H$_4$-CH$_2$OH | A | 4-MeO-C$_6$H$_4$-CHO | 91% (2.5 h) |
| 14 | PhCH(OH)CH(OH)Ph | A | PhC(O)C(O)Ph | 99% (4 h) |

Example 5

Oxidation of Alcohols Using Hypochlorous Acid as Bulk Oxidant (a) Oxidation of L-Menthol

[Formula 7]

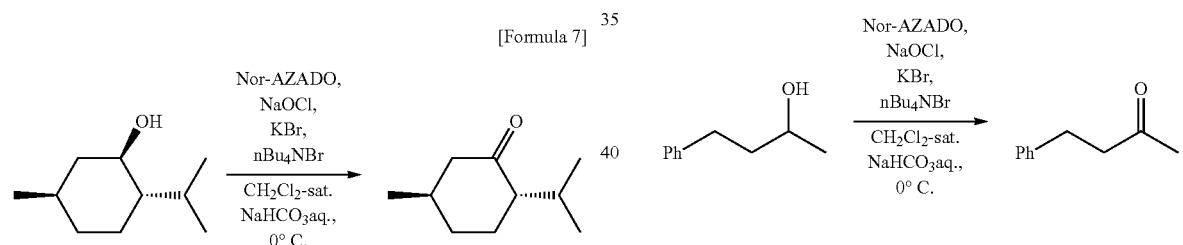

A solution of L-menthol (94.4 mg, 0.604 mmol) in dichloromethane (1.61 ml) was added with a solution of potassium bromide (7.2 mg, 0.060 mmol) and tetrabutylammonium bromide (11.1 mg, 0.030 mmol) in saturated aqueous sodium hydrogencarbonate (604 μl) and Nor-AZADO (0.83 mg, 6.04 μmol), and the mixture was cooled on ice. The reaction mixture was slowly added dropwise with a 2.09 M aqueous solution of sodium hypochlorite (434 μl, 0.906 mmol) in saturated aqueous sodium hydrogencarbonate (1.01 ml), and the mixture was stirred at the same temperature for 20 minutes. The reaction mixture was added with saturated aqueous sodium sulfite (2 ml), and the mixture was extracted with dichloromethane. The organic layer was dried over sodium sulfate, and then concentrated under reduced pressure. The residue was purified by silica gel column chromatography to obtain the objective compound (88.7 mg; yield, 95.2%).

$^1$H-NMR (400 MHz, CDCl$_3$): δ 2.35 (ddd, J=12.8, 3.7, 2.3 Hz, 1H), 2.18-1.81 (m, 6H), 1.43-1.29 (m, 2H), 1.01 (d, J=6.3 Hz, 3H), 0.91 (d, J=6.8 Hz, 3H), 0.85 (d, J=6.8 Hz, 3H).

$^{13}$C-NMR (100 MHz, CDCl$_3$): δ 212.3, 55.8, 50.8, 35.4, 33.9, 27.8, 25.8, 22.2, 21.2, 18.6.

IR (neat, cm$^{-1}$): 1711.

EI-MS m/z: 154 (M$^+$).

HRMS (EI): Calcd. for C$_{10}$H$_{18}$O: 154.1358, Found: 154.1343.

(b) Oxidation of 4-phenylbutan-2-ol

[Formula 8]

Ph〜CH(OH)CH$_3$ →(Nor-AZADO, NaOCl, KBr, nBu$_4$NBr, CH$_2$Cl$_2$-sat. NaHCO$_3$aq., 0° C.)→ Ph〜C(O)CH$_3$ 4-Phenylbutan-2-ol (104.3 mg, 0.694 mmol) was oxidized in the same manner as that described in Example 5, (a) to obtain the objective compound (101.0 mg, 98.7%).

$^1$H-NMR (400 MHz, CDCl$_3$): δ 7.30-7.16 (m, 5H), 2.92-2.98 (m, 2H), 2.78-2.74 (m, 2H), 2.14 (s, 3H).

$^{13}$C-NMR (100 MHz, CDCl$_3$): δ 207.8, 140.9, 128.4, 128.2, 126.0, 45.1, 30.0, 29.6.

IR (neat, cm$^{-1}$): 1717.

EI-MS m/z: 148 (M$^+$).

HRMS (EI): Calcd. for C$_{10}$H$_{12}$O: 148.0888, Found: 148.0873.

(c) Oxidation of 4-phenylbutanol

[Formula 9]

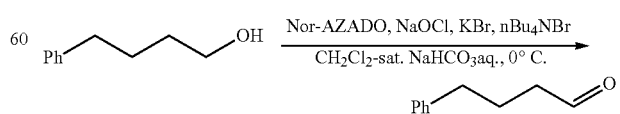

4-Phenylbutanol (99.2 mg, 0.660 mmol) was oxidized in the same manner as that described in Example 5, (a) to obtain the objective compound (89.9 mg, 91.9%).

¹H-NMR (400 MHz, CDCl₃): δ 9.74 (d, J=1.5 Hz, 1H), 7.30-7.15 (m, 5H), 2.65 (t, J=7.7 Hz, 2H), 2.43 (dt, J=7.2, 1.5 Hz, 2H), 1.95 (tt, J=7.7, 7.2 Hz).

¹³C-NMR (100 MHz, CDCl₃): δ 202.2, 141.2, 128.4, 128.3, 126.0, 43.1, 34.9, 23.6.

IR (neat, cm⁻¹): 1724.

EI-MS ra/z: 148 (M⁺).

HRMS (EI): Calcd. for C₁₀H₁₂O: 148.0888, Found: 148.0873.

Example 6

Oxidation of Alcohols Using Air as Bulk Oxidant (a) Oxidation of 4-phenylbutan-2-ol

[Formula 10]

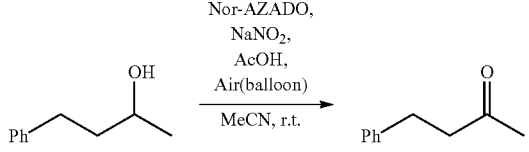

A solution of 4-phenylbutan-2-ol (104.3 mg, 0.694 mmol), Nor-AZADO (0.96 mg, 6.94 μmol), and acetic acid (79.5 μl, 1.389 mmol) in acetonitrile (0.69 ml) was added with sodium nitrite (9.58 mg, 0.139 mmol), and the mixture was stirred at room temperature for 4 hours under an air atmosphere. The reaction mixture was added with saturated aqueous sodium carbonate (2 ml), and the mixture was extracted with dichloromethane. The organic layer was dried over sodium sulfate, and then concentrated under reduced pressure. The residue was purified by silica gel column chromatography to obtain the objective compound (101.1 mg; yield, 98.3%). The spectrum data were found to be the same as those obtained in Example 5, (b).

(b) Oxidation of L-Menthol

[Formula 11]

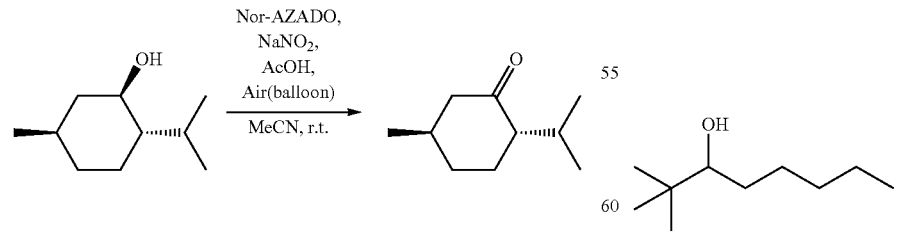

L-Menthol (100.7 mg, 0.644 mmol) was oxidized in the same manner as that described in Example 6, (a) to obtain the objective compound (95.4 mg; yield, 96.0%). The spectrum data were found to be the same as those obtained in Example 5, (a).

(c) Oxidation of (+)-Fenchyl Alcohol

[Formula 12]

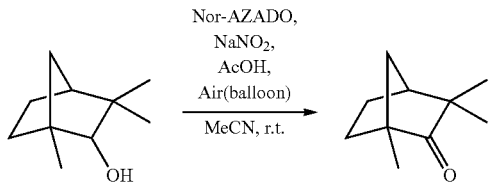

(+)-Fenchyl alcohol (103.0 mg, 0.668 mmol) was oxidized in the same manner as that described in Example 6, (a) to obtain the objective compound (93.0 mg; yield, 91.5%).

¹H-NMR (400 MHz, CDCl₃): δ 2.14 (brs, 1H), 1.81-1.68 (m, 3H), 1.60-1.52 (m, 2H), 1.42-1.35 (m, 1H), 1.15 (d, J=1.7 Hz, 3H), 1.04 (s, 3H), 1.04 (s, 3H).

¹³C-NMR (100 MHz, CDCl₃): δ 223.4, 54.1, 47.3, 45.3, 41.6, 31.8, 24.9, 23.3, 21.7, 14.6.

IR (neat, cm⁻¹): 1740.

EI-MS m/z: 152 (M⁺).

HRMS (EI): Calcd. for C₁₀H₁₆O: 152.1201, Found: 152.1205.

(d) Oxidation of 2,2-dimethyl-1-phenylpropanol

[Formula 13]

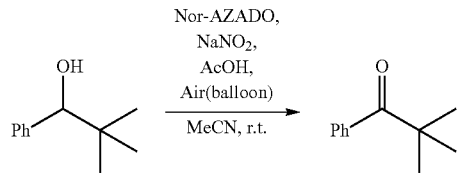

2,2-Dimethyl-1-phenylpropanol (71.4 mg, 0.435 mmol) was oxidized in the same manner as that described in Example 6, (a) to obtain the objective compound (67.2 mg; yield, 95.3%).

¹H-NMR (400 MHz, CDCl₃): δ 7.68 (d, J=7.3 Hz, 2H), 7.48-7.38 (m, 3H), 1.35 (s, 9H).

¹³C-NMR (100 MHz, CDCl₃): δ 209.2, 138.6, 130.7, 128.0, 127.8, 44.1, 28.0.

IR (neat, cm⁻¹): 1676.

EI-MS m/z: 162 (M⁺).

HRMS (EI): Calcd. for C₁₁H₁₄O: 162.1045, Found: 162.1050.

(e) Oxidation of 2,2-dimethyloctan-3-ol

[Formula 14]

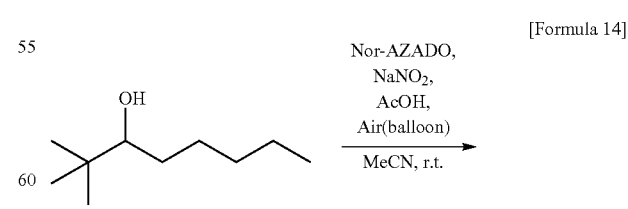

2,2-Dimethyloctan-3-ol (80.7 mg, 0.510 mmol) was oxidized in the same manner as that described in Example 6, (a) to obtain the objective compound (69.4 mg; yield, 87.1%).

$^1$H-NMR (400 MHz, CDCl$_3$): δ 2.46 (t, J=7.2 Hz, 2H), 1.59-1.51 (m, 2H), 1.34-1.24 (m, 4H), 1.24 (s, 9H), 0.89 (t, J=7.2 Hz, 3H).

$^{13}$C-NMR (100 MHz, CDCl$_3$): δ 216.1, 44.1, 36.4, 31.5, 26.4, 23.6, 22.6, 13.9.

IR (neat, cm$^{-1}$): 1733.

EI-MS m/z: 156 (M$^+$).

HRMS (M): Calcd. for C$_{10}$H$_{20}$O: 156.1514, Found: 156.1500.

(f) Oxidation of trans-2-phenylcyclohexanol

[Formula 15]

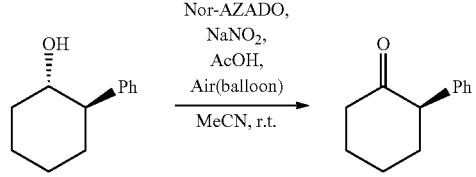

trans-2-Phenylcyclohexanol (63.4 mg, 0.360 mmol) was oxidized in the same manner as that described in Example 6, (a) to obtain the objective compound (62.4 mg; yield, 99.4%).

$^1$H-NMR (400 MHz, CDCl$_3$): δ 7.35-7.13 (m, 5H), 3.61 (dd, J=12.1, 5.3 Hz, 1H), 2.53-2.45 (m, 2H), 2.30-2.25 (m, 1H), 2.17-2.15 (m, 1H), 2.06-1.99 (m, 2H), 1.86-1.80 (m, 2H).

$^{13}$C-NMR (100 MHz, CDCl$_3$): δ 210.2, 138.7, 128.5, 128.3, 126.8, 57.3, 42.1, 35.0, 27.8, 25.3.

IR (CHCl$_3$, cm$^{-1}$): 1700.

EI-MS m/z: 174 (M$^+$)

HRMS (EI): Calcd. for C$_{12}$H$_{14}$O: 174.1045, Found: 174.1058.

(g) Oxidation of 1,2:4,5-di-O-isopropylidene-β-fructopyranose

[Formula 16]

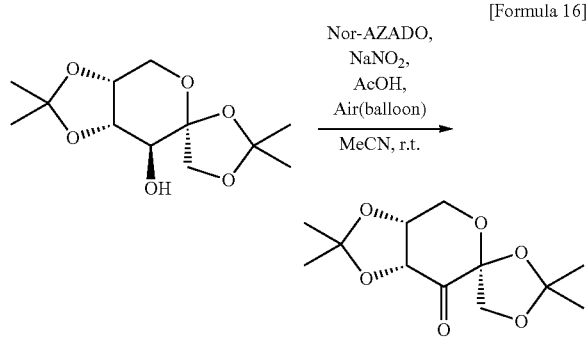

1,2:4,5-Di-O-isopropylidene-β-fructopyranose (102.2 mg, 0.393 mmol) was oxidized in the same manner as that described in Example 6, (a) to obtain the objective compound (91.6 mg; yield, 90.3%).

$^1$H-NMR (400 MHz, CDCl$_3$): δ 4.73 (d, J=5.6 Hz, 1H), 4.61 (d, J=9.4 Hz, 1H), 4.53 (m, 1H), 4.39 (dd, J=13.5, 2.2 Hz, 1H), 4.12 (d, J=13.5 Hz, 1H), 4.00 (d, J=9.4 Hz, 1H), 1.55 (s, 3H), 1.47 (s, 3H), 1.40 (s, 6H).

$^{13}$C-NMR (100 MHz, CDCl$_3$): δ 196.9, 113.8, 110.6, 104.1, 77.9, 75.9, 70.0, 60.1, 27.1, 26.5, 26.0, 26.0

IR (neat, cm$^{-1}$): 1749.

EI-MS m/z: 259 (M$^+$+H).

HRMS (EI): Calcd. for C$_{12}$H$_{19}$O$_6$: 259.1182, Found: 259.1164.

(h) Oxidation of 2-(1-hydroxyethyl)pyridine

[Formula 17]

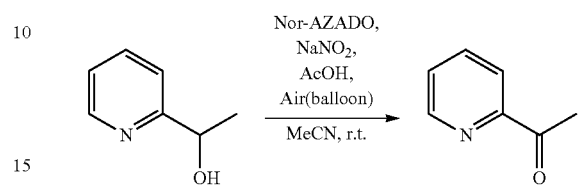

2-(1-Hydroxyethyl)pyridine (105.4 mg, 0.856 mmol) was oxidized in the same manner as that described in Example 6, (a) to obtain the objective compound (83.6 mg; yield, 80.6%).

$^1$H-NMR (400 MHz, CDCl$_3$): δ 8.69 (brd, J=4.1 Hz, 1H), 8.05 (d, J=8.0 Hz, 1H), 7.84 (td, J=7.7, 1.7 Hz, 1H), 7.49-7.30 (m, 1H), 2.73 (s, 3H).

$^{13}$C-NMR (100 MHz, CDCl$_3$): δ 200.0, 153.6, 148.9, 136.8, 127.0, 121.6, 25.7.

IR (neat, cm$^{-1}$): 1700.

EI-MS m/z: 121 (M$^+$).

HRMS (EI): Calcd. for C$_7$H$_7$NO: 121.0528, Found: 121.0529.

(i) Oxidation of 4-phenylbutanol

[Formula 18]

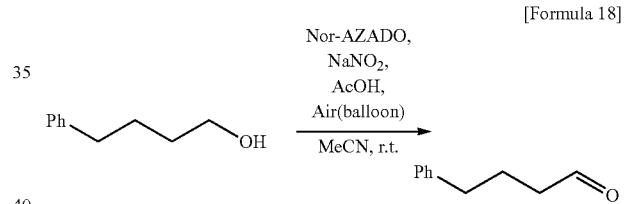

4-Phenylbutanol (103.6 mg, 0.690 mmol) was oxidized in the same manner as that described in Example 6, (a) to obtain the objective compound (91.0 mg; yield, 89.1%). The spectrum data were found to be the same as those obtained in Example 5, (c).

(j) Oxidation of 4-methoxybenzyl alcohol

[Formula 19]

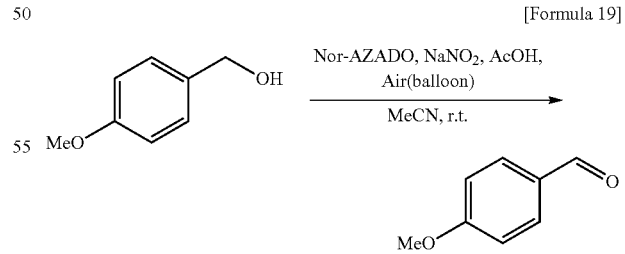

4-Methoxybenzyl alcohol (96.0 mg, 0.695 mmol) was oxidized in the same manner as that described in Example 6, (a) to obtain the objective compound (85.9 mg; yield, 90.8%).

$^1$H-NMR (400 MHz, CDCl$_3$): δ 9.89 (s, 1H), 7.84 (d, J=8.7 Hz, 2H), 7.01 (d, J=8.4 Hz, 2H), 3.89 (s, 3H).

$^{13}$C-NMR (100 MHz, CDCl$_3$): δ 190.7, 164.6, 131.9, 129.9, 114.3, 55.5.

(k) Oxidation of Hydrobenzoin

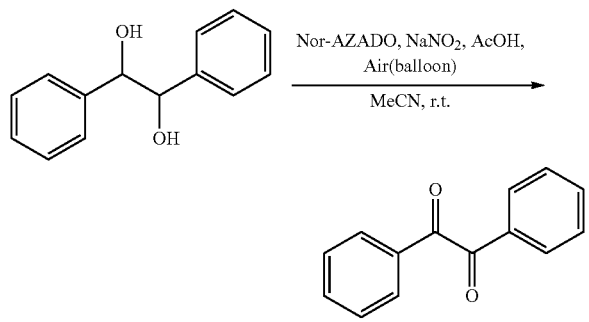

[Formula 20]

Hydrobenzoin (81.6 mg, 0.381 mmol) was oxidized in the same manner as that described in Example 6, (a) to obtain the objective compound (79.5 mg; yield, 99.3%).

$^1$H-NMR (400 MHz, CDC$_{l3}$): δ 7.99-7.96 (m, 4H), 7.68-7.63 (m, 2H), 7.53-7.49 (t, J=7.7 Hz, 4H).

$^{13}$C-NMR (100 MHz, CDCl$_3$): δ 194.5, 134.9, 133.0, 129.9, 129.0.

IR(CHCl$_3$, cm$^{-1}$): 1660.

EI-MS m/z: 210 (M$^+$).

HRMS (EI): Calcd. for C$_{14}$H$_{10}$O$_2$: 210.0681, Found: 210.0679.

(l) Oxidation of 2-adamantanol

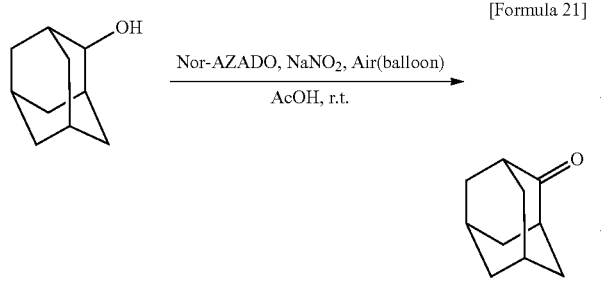

[Formula 21]

A solution of 2-adamantanol (101.1 mg, 0.664 mmol) and Nor-AZADO (0.92 mg, 6.64 μmol) in acetic acid (2.0 ml) was added with sodium nitrite (9.2 mg, 0.133 mmol), and the mixture was stirred at room temperature for 22 hours under an air atmosphere. The reaction mixture was added with saturated aqueous sodium carbonate (10 ml), and the mixture was extracted with dichloromethane. The organic layer was dried over sodium sulfate, and then concentrated under reduced pressure. The residue was purified by silica gel column chromatography to obtain the objective compound (91.8 mg; yield, 92.0%).

$^1$H-NMR (400 MHz, CDCl$_3$): δ 2.55 (s, 2H), 2.10-1.94 (m, 12H).

$^{13}$C-NMR (100 MHz, CDCl$_3$): δ 218.4, 47.0, 39.2, 36.1, 27.4.

IR (neat, cm$^{-1}$): 1719.

EI-MS m/z: 150 (M$^+$).

HRMS (EI): Calcd. for C$_{10}$H$_{14}$O: 150.1045, Found: 150.1049.

(m) Oxidation of trans-4-carbobenzyloxyaminocyclohexanol

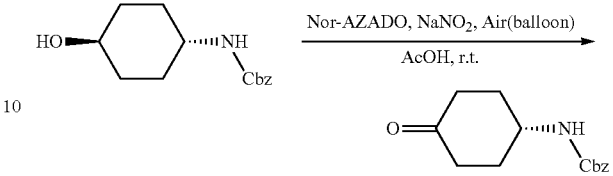

[Formula 22]

trans-4-Carbobenzyloxyaminocyclohexanol (100.6 mg, 0.404 mmol) was oxidized in the same manner as that described in Example 6, (l) to obtain the objective compound (73.3 mg; yield, 73.4%).

$^1$H-NMR (400 MHz, CDCl$_3$): δ 7.37-7.31 (m, 5H), 5.12 (s, 2H), 4.75 (br s, 1H), 3.99 (br s, 1H), 2.45-2.40 (m, 4H), 2.28-2.24 (m, 2H), 1.75-1.59 (m, 2H).

$^{13}$C-NMR (100 MHz, CDCl$_3$): δ 209.5, 155.6, 136.3, 128.5, 128.2, 128.1, 66.8, 47.9, 38.8, 32.1.

IR (neat, cm$^{-1}$): 1704, 1530.

EI-MS m/z: 247 (M$^+$).

HRMS (EI): Calcd. for C$_{14}$H$_{17}$NO$_3$: 247.1208, Found: 247.1206.

(n) Oxidation of 2',5'-bis-O-(t-butyldimethylsilyl)-β-D-adenosine

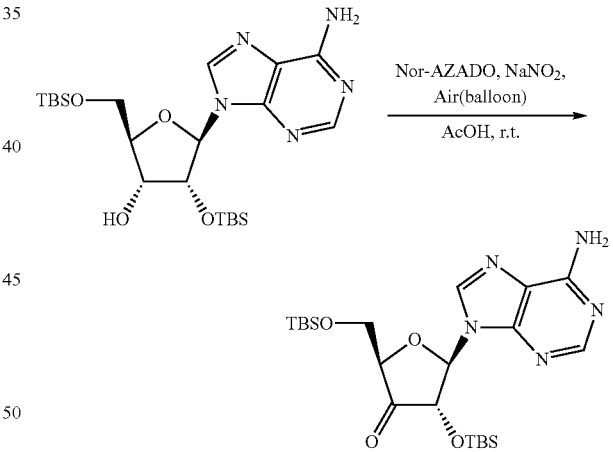

[Formula 23]

2',5'-Bis-O-(t-butyldimethylsilyl)-β-D-adenosine (83.8 mg, 0.169 mmol) was oxidized in the same manner as that described in Example 6, (l) to obtain the objective compound (66.8 mg; yield, 80.0%).

$^1$H-NMR (400 MHz, CDCl$_3$): δ 8.36 (s, 1H), 8.14 (s, 1H), 6.13 (d, J=8.2 Hz, 1H), 5.85 (br s, 2H), 4.94 (d, J=8.2 Hz, 2H), 4.29 (br s, 1H), 3.97 (m, 2H) 0.92 (s, 9H), 0.72 (s, 9H), 0.10 (s, 3H), 0.07 (s, 3H), −0.02 (s, 3H), −0.20 (s, 3H).

$^{13}$C-NMR (100 MHz, CDCl$_3$): δ 208.6, 155.5, 153.4, 150.4, 138.5, 119.8, 85.0, 82.4, 77.8, 62.4, 25.8, 25.3, 18.2, 18.0, −4.8, −5.5, −5.6, −5.7.

IR (neat, cm$^{-1}$): 1788, 1647, 1595, 1577.

EI-MS m/z: 436 (M$^+$-tBu).

HRMS (EI): Calcd. for $C_{22}H_{39}N_5O_4Si_2$: 493.2541, Found: 493.2511.

Example 7

Oxidation of Alcohols Using Aqueous Hydrogen Peroxide as Bulk Oxidant (a) Oxidation of 4-phenylbutan-2-ol

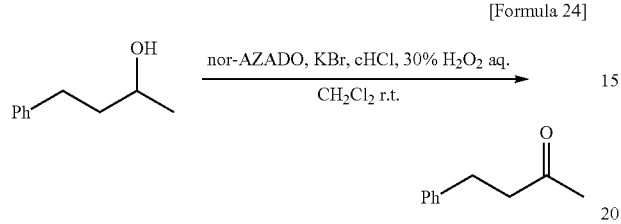

[Formula 24]

A solution of 4-phenylbutan-2-ol (100.1 mg, 0.666 mmol), Nor-AZADO (0.92 mg, 6.66 µmol), potassium bromide (39.7 mg, 0.333 mmol) and hydrochloric acid (11.1 µl, 0.133 mmol) in dichloromethane (0.67 ml) was added with 30% aqueous hydrogen peroxide (102.1 µl, 1.000 mmol), and the mixture was stirred at room temperature for 4 hours. The reaction mixture was added with saturated aqueous sodium carbonate (2 ml) and saturated aqueous sodium thiosulfate (2 ml), and the mixture was stirred at room temperature for 2 hours, and then extracted with dichloromethane. The organic layer was dried over sodium sulfate, and then concentrated under reduced pressure. The residue was purified by silica gel column chromatography to obtain the objective compound (95.3 mg; yield, 96.5%). The spectrum data were found to be the same as those obtained in Example 5, (b).

(b) Oxidation of 4-nitrobenzyl alcohol

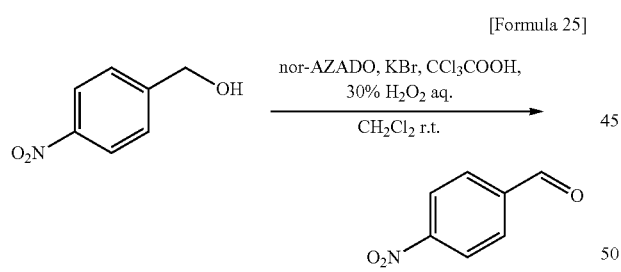

[Formula 25]

A solution of 4-nitrobenzyl alcohol (98.6 mg, 0.644 mmol), Nor-AZADO (0.89 mg, 6.44 µmol), potassium bromide (15.3 mg, 0.129 mmol) and trichloroacetic acid (105.2 mg, 0.644 mmol) in dichloromethane (1.29 ml) was added with 30% aqueous hydrogen peroxide (328.8 µl, 3.22 mmol), and the mixture was stirred at room temperature for 6 hours. The reaction mixture was added with saturated aqueous sodium carbonate (2 ml) and saturated aqueous sodium thiosulfate (2 ml), and the mixture was stirred at room temperature for 30 minutes, and then extracted with dichloromethane. The organic layer was dried over sodium sulfate, and then concentrated under reduced pressure. The residue was purified by silica gel column chromatography to obtain the objective compound (90.0 mg; yield, 92.5%).

$^1$H-NMR (400 MHz, CDCl$_3$): δ 10.16 (s, 1H), 8.40 (dd, J=8.8, 1.8 Hz, 2H), 8.08 (dd, J=8.8, 1.8 Hz, 2H).

$^{13}$C-NMR (100 MHz, DMSO-d$_6$): δ 192.3, 150.6, 140.1, 130.6, 124.2.

IR (neat, cm$^{-1}$): 1709, 1537.

EI-MS m/z: 131 (M$^+$).

HRMS (EI): Calcd. for $C_7H_5NO_3$: 151.0269, Found: 151.0253.

Example 8

Oxidation of Alcohols Using Diisopropyl Dicarboxylate (DIAD) as Bulk Oxidant (a) Oxidation of 4-phenylbutan-2-ol

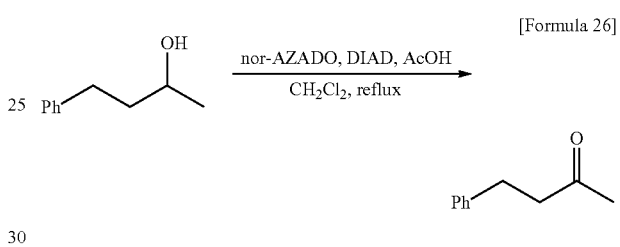

[Formula 26]

A solution of 4-phenylbutan-2-ol (97.7 mg, 0.651 mmol), Nor-AZADO (0.90 mg, 6.51 µmol, 1 mol %) and acetic acid (37 µl, 0.651 mmol) in dichloromethane (0.65 ml) was added with DIAD (128 µl, 0.651 mmol, 1 equivalent), and the mixture was stirred for 8 hours under reflux by heating. The reaction mixture was added with saturated aqueous sodium carbonate (2 ml), and the mixture was extracted with dichloromethane. The organic layer was dried over sodium sulfate, and then concentrated under reduced pressure. The residue was purified by silica gel column chromatography to obtain the objective compound (95.1 mg; yield, 99%). The spectrum data were found to be the same as those obtained in Example 5, (b).

(b) Oxidation of Menthol

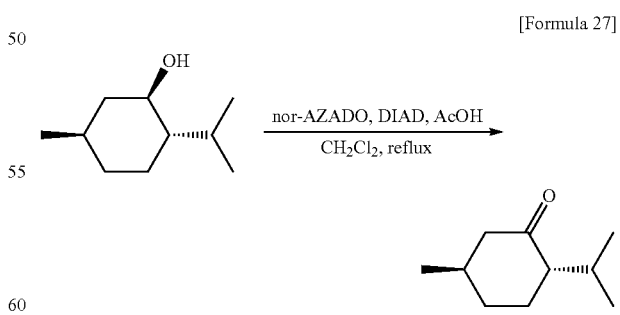

[Formula 27]

L-Menthol (79.6 mg, 0.509 mmol) was oxidized in the same manner as that described in Example 8, (a) (except that Nor-AZADO was used at 3 mol %) to obtain the objective compound (70.7 mg; yield, 90.0%). The spectrum data were found to be the same as those obtained in Example 5, (a).

(c) Oxidation of 2,2-dimethyl-1-phenylpropanol

[Formula 28]

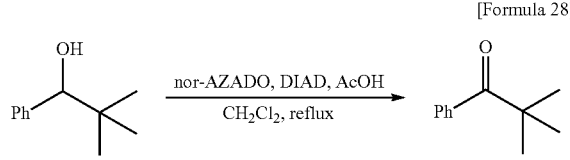

2,2-Dimethyl-1-phenylpropanol (105.7 mg, 0.644 mmol) was oxidized in the same manner as that described in Example 8, (a) to obtain the objective compound (91.0 mg; yield, 87.2%). The spectrum data were found to be the same as those obtained in Example 6, (d).

(d) Oxidation of 1,2:4,5-di-O-isopropylidene-β-fructopyranose

[Formula 29]

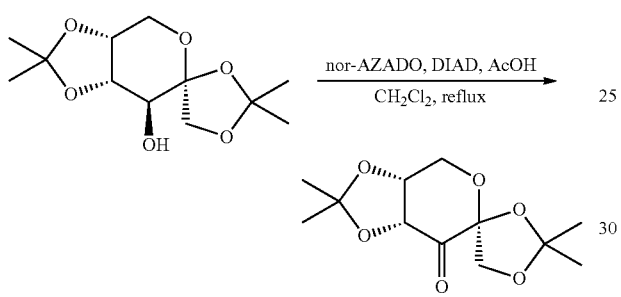

1,2:4,5-Di-O-isopropylidene-β-fructopyranose (132.8 mg, 0.510 mmol) was oxidized in the same manner as that described in Example 8, (a) to obtain the objective compound (120.4 mg; yield, 91.3%). The spectrum data were found to be the same as those obtained in Example 6, (g).

(e) Oxidation of trans-4-carbobenzyloxyaminocyclohexanol

[Formula 30]

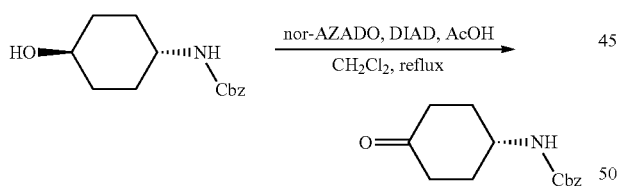

trans-4-Carbobenzyloxyaminocyclohexanol (119.2 mg, 0.478 mmol) was oxidized in the same manner as that described in Example 8, (a) (except that Nor-AZADO was used at 3 mol %, and DIAD was used in an amount of 1.1 equivalents) to obtain the objective compound (106.8 mg; yield, 90.3%). The spectrum data were found to be the same as those obtained in Example 6, (m).

(f) Oxidation of 4-phenylbutanol

[Formula 31]

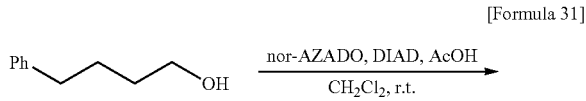

-continued

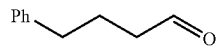

4-Phenylbutanol (79.3 mg, 0.528 mmol) was oxidized in the same manner as that described in Example 8, (a) (except that Nor-AZADO was used at 3 mol %, and the reaction was performed at room temperature) to obtain the objective compound (67.0 mg; yield, 85.6%). The spectrum data were found to be the same as those obtained in Example 5, (c).

(g) Oxidation of 4-nitrobenzyl alcohol

[Formula 32]

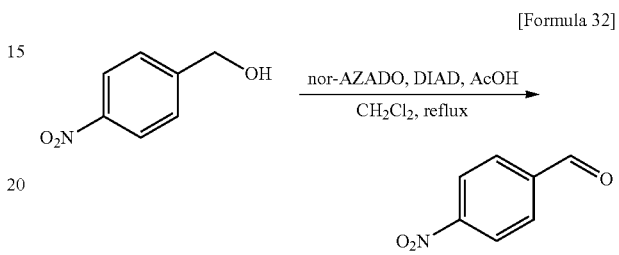

4-Nitrobenzyl alcohol (75.5 mg, 0.493 mmol) was oxidized in the same manner as that described in Example 8, (a) to obtain the objective compound (72.6 mg; yield, 97.5%). The spectrum data were found to be the same as those obtained in Example 7, (b).

(h) Oxidation of 4-methoxybenzyl alcohol

[Formula 33]

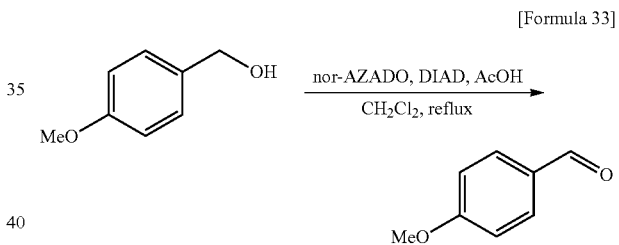

4-Methoxybenzyl alcohol (78.3 mg, 0.566 mmol) was oxidized in the same manner as that described in Example 8, (a) to obtain the objective compound (71.3 mg; yield, 92.5%). The spectrum data were found to be the same as those obtained in Example 6, (j).

(i) Oxidation of 2,4-dimethoxybenzyl alcohol

[Formula 34]

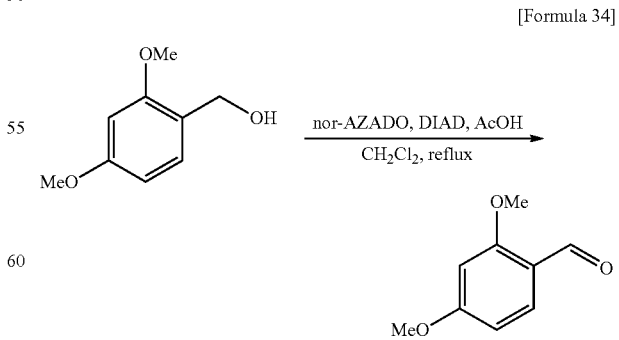

2,4-Dimethoxybenzyl alcohol (84.8 mg, 0.504 mmol) was oxidized in the same manner as that described in Example 8, (a) to obtain the objective compound (77.2 mg; yield, 92.1%).

$^1$H-NMR (400 MHz, CDCl$_3$): δ 10.30 (s, 1H), 7.82 (d, J=8.7 Hz, 1H), 6.55 (dd, J=8.4, 2.9 Hz, 1H), 6.45 (d, J=2.9 Hz, 1H), 3.91 (s, 3H), 3.88 (s, 3H).

$^{13}$C-NMR (100 MHz, CDCl$_3$): δ 188.3, 166.2, 163.6, 130.7, 119.1, 105.7, 97.9, 55.6, 55.6.

IR (neat, cm$^{-1}$): 1670, 1266; MS m/z: 166 (M$^+$).

HRMS (EI): Calcd. for C$_9$H$_{10}$O$_3$: 166.0630, Found: 166.0625.

(j) Oxidation of 2,4,6-trimethylbenzyl alcohol

[Formula 35]

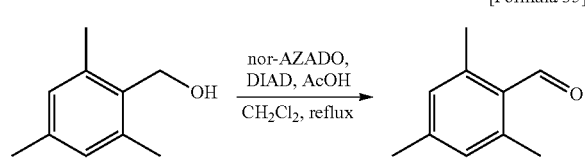

2,4,6-Trimethylbenzyl alcohol (92.5 mg, 0.616 mmol) was oxidized in the same manner as that described in Example 8, (a) to obtain the objective compound (87.2 mg; yield, 95.5%).

$^1$H-NMR (400 MHz, CDCl$_3$): δ 10.57 (s, 1H), 6.90 (s, 2H), 2.60 (s, 6H), 2.32 (s, 3H).

$^{13}$C-NMR (100 MHz, CDCl$_3$): δ 192.9, 143.8, 141.4, 130.5, 130.0, 21.4, 20.5.

IR (neat, cm$^{-1}$): 1686; MS m/z: 148 (M$^+$).

HRMS (EI): Calcd. for C$_{10}$H$_{12}$O: 148.0888, Found: 148.0878.

(k) Oxidation of 4-bromobenzyl alcohol

[Formula 36]

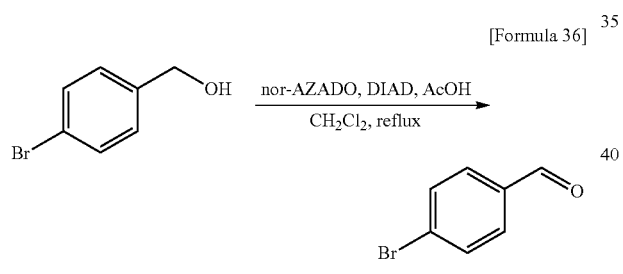

4-Bromobenzyl alcohol (98.9 mg, 0.529 mmol) was oxidized in the same manner as that described in Example 8, (a) to obtain the objective compound (91.3 mg; yield, 93.3%).

$^1$H-NMR, (400 MHz, CDCl$_3$): δ 9.98 (s, 1H), 7.75 (d, J=8.7 Hz, 1H), 7.69 (d, J=8.2 Hz, 1H).

$^{13}$C-NMR (100 MHz, CDCl$_3$): δ 191.0, 135.1, 132.4, 132.4, 130.9, 129.8.

IR (neat, cm$^{-1}$): 1688, 1066; MS m/z: 184 (M$^+$), 183 (M$^{+-}$H).

HRMS (EI): Calcd. for C$_7$H$_5$BrO: 183.9524, Found: 183.9523.

(l) Oxidation of 4-methylthiobenzyl alcohol

[Formula 37]

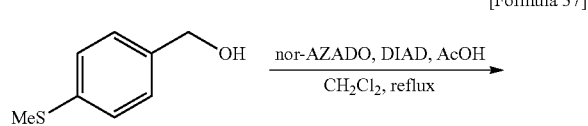

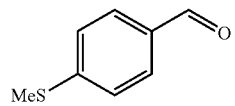

4-Methylthiobenzyl alcohol (91.7 mg, 0.594 mmol) was oxidized in the same manner as that described in Example 8, (a) to obtain the objective compound (83.7 mg; yield, 92.5%).

$^1$H-NMR (400 MHz, CDCl$_3$): δ 9.92 (s, 1H), 7.77 (d, J=8.7 Hz, 1H), 7.33 (d, J=8.2 Hz, 1H), 2.54 (s, 3H).

$^{13}$C-NMR (100 MHz, CDCl$_3$): δ 191.2, 147.9, 133.0, 130.0, 125.2, 14.7.

IR (neat, cm$^{-1}$): 1695; MS m/z: 152 (M$^+$).

HRMS (EI): Calcd. for C$_8$H$_8$OS: 152.0296, Found: 152.0290.

(m) Oxidation of 2',5'-bis-O-(t-butyldimethylsilyl)-β-D-adenosine

[Formula 38]

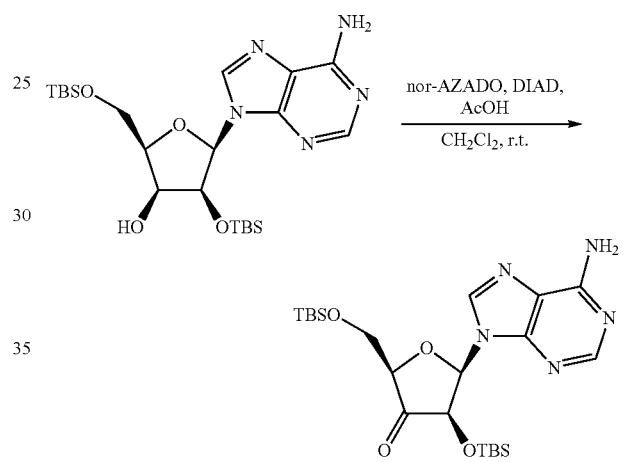

2',5'-Bis-O-(t-butyldimethylsilyl)-β-D-adenosine (53.0 mg, 0.107 mmol) was oxidized in the same manner as that described in Example 8, (a) (except that Nor-AZADO was used at 10 mol %, DIAD was used in an amount of 1.2 equivalents, and the reaction was performed at room temperature) to obtain the objective compound (35.8 mg; yield, 67.8%). The spectrum data were found to be the same as those obtained in Example 6, (n).

(n) Oxidation of 3-quinuclidinol

[Formula 39]

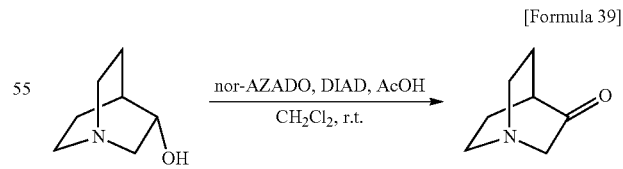

3-Quinuclidinol (43.1 mg, 0.339 mmol) was oxidized in the same manner as that described in Example 8, (a) (except that Nor-AZADO was used at 10 mol %, DIAD was used in an amount of 1.2 equivalents, and the reaction was performed at room temperature) to obtain the objective compound (36.7 mg; yield, 86.5%).

$^1$H-NMR (400 MHz, CDCl$_3$): δ 3.30 (s, 2H), 3.07-2.89 (m, 4H), 2.46 (quin, J=3.0 Hz, 1H), 2.03-1.98 (m, 4H).

$^{13}$C-NMR (100 MHz, CDCl$_3$): δ 219.6, 62.8, 46.9, 39.6, 25.6.

IR (neat, cm$^{-1}$): 1725. MS m/z 125 (M$^+$).

HRMS (EI) Calcd. for C$_7$H$_{11}$O: 125.0841, found: 125.0834.

(o) Oxidation of 2-(1-hydroxyethyl)pyridine

[Formula 40]

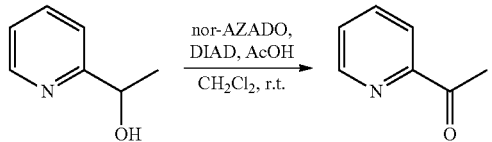

2-(1-Hydroxyethyl)pyridine (76.8 mg, 0.624 mmol) was oxidized in the same manner as that described in Example 8, (a) (except that Nor-AZADO was used at 3 mol %, and the reaction was performed at room temperature) to obtain the objective compound (66.0 mg; yield, 87.4%). The spectrum data were found to be the same as those obtained in Example 6, (h).

(o) Oxidation of 2-(1-hydroxyethyl)thiophene

[Formula 41]

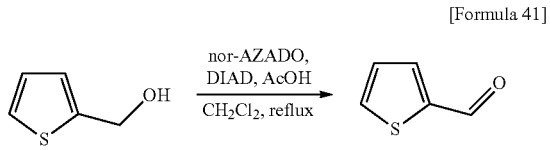 [SMILES: OCc1cccs1 ; O=Cc1cccs1]

2-(1-Hydroxyethyl)thiophene (64.9 mg, 0.569 mmol) was oxidized in the same manner as that described in Example 8, (a) to obtain the objective compound (56.5 mg; yield, 88.6%).

$^1$H-NMR (400 MHz, CDCl$_3$): δ 9.96 (d, J=1.0 Hz, 1H), 7.80-7.77 (m, 2H), 7.22 (dd, J=4.8, 3.9 Hz, 1H), 7.33 (d, J=8.2 Hz, 1H), 2.54 (s, 3H).

$^{13}$C-NMR (100 MHz, CDCl$_3$): δ 182.9, 144.1, 136.2, 135.1, 128.3.

IR (neat, cm$^{-1}$): 1672, 1419, 729; MS m/z: 112 (M$^+$).

HRMS (EI): Calcd. for C$_5$H$_4$OS: 111.9983, Found: 111.9935.

(p) Oxidation of cinnamyl alcohol

[Formula 42]

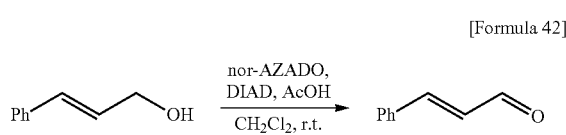

Cinnamyl alcohol (80.7 mg, 0.601 mmol) was oxidized in the same manner as that described in Example 8, (a) (except that DIAD was used in an amount of 1.2 equivalents, and the reaction was performed at room temperature) to obtain the objective compound (77.8 mg; yield, 97.9%).

$^1$H-NMR (400 MHz, CDCl$_3$): δ 9.72 (d, J=7.8 Hz, 1H), 7.59-7.56 (m, 2H), 7.49-7.42 (m, 4H), 6.74 (dd, J=15.9, 7.7 Hz, 2H).

$^{13}$C-NMR (100 MHz, CDCl$_3$): δ 193.7, 152.7, 134.0, 131.2, 129.1, 128.6, 128.5.

IR(CHCl$_3$, cm$^{-1}$): 1681; MS m/z: 132 (M$^+$).

HRMS (EI): Calcd. for C$_9$H$_8$O: 132.0575, found: 132.0558.

(q) Oxidation of 2-octenol

[Formula 43]

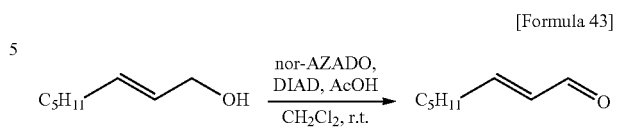

2-Octenol (58.2 mg, 0.454 mmol) was oxidized in the same manner as that described in Example 8, (a) (except that Nor-AZADO was used at 3 mol %, and the reaction was performed at room temperature) to obtain the objective compound (50.0 mg; yield, 87.3%).

$^1$H-NMR (400 MHz, CDCl$_3$): δ 9.51 (d, J=7.7 Hz, 1H), 6.85 (dt, J=15.5, 6.8 Hz, 1H), 6.12 (ddt, J=15.5, 7.7, 1.4 Hz, 1H), 2.36-2.31 (m, 2H), 1.55-1.28 (m, 2H), 1.37-1.30 (m, 4H), 0.92-0.89 (m, 3H).

$^{13}$C-NMR (100 MHz, CDCl$_3$): δ 194.1, 158.9, 133.0, 32.7, 31.3, 27.5, 22.4, 13.9.

IR (neat, cm$^{-1}$): 1693, 1637; MS m/z: 116 (M$^+$).

HRMS (EI): Calcd. for C$_8$H$_{14}$O: 126.1045, Found: 126.1050.

(r) Oxidation of 9-decenol

[Formula 44]

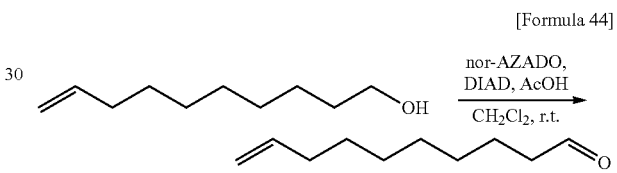

9-Decenol (69.0 mg, 0.441 mmol) was oxidized in the same manner as that described in Example 8, (a) (except that Nor-AZADO was used at 3 mol %, and the reaction was performed at room temperature) to obtain the objective compound (57.9 mg; yield, 85.0%).

$^1$H-NMR (400 MHz, CDCl$_3$): δ 9.77 (d, J=1.9 Hz, 1H), 5.86-5.75 (m, 1H), 5.02-4.92 (m, 2H), 2.42 (dt, J=7.2, 1.9 Hz, 2H), 2.04 (tt, J=7.7, 7.2 Hz, 2H), 1.65-1.61 (m, 2H), 1.40-1.32 (m, 8H).

$^{13}$C-NMR (100 MHz, CDCl$_3$): δ 202.8, 139.0, 114.2, 43.9, 33.7, 29.2, 29.1, 28.8, 28.8, 22.0.

IR (neat, cm$^{-1}$): 1727, 1640; MS ink: 154 (M$^+$).

HRMS (EI); Calcd. for C$_{10}$H$_{18}$O: 154.1358, Found: 154.1369.

(r) Oxidation of trans-3,7-dimethyl-2,6-octadienol

[Formula 45]

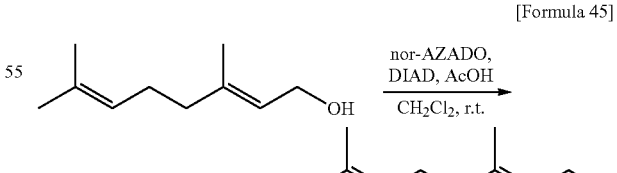

trans-3,7-Dimethyl-2,6-octadienol (78.3 mg, 0.508 mmol) was oxidized in the same manner as that described in Example 8, (a) (except that Nor-AZADO was used at 3 mol %, DIAD was used in an amount of 1.1 equivalents, and the reaction was performed at room temperature) to obtain the objective compound (66.9 mg; yield, 86.6%).

$^1$H-NMR, (400 MHz, CDCl$_3$): δ 9.99 (d, J=7.7 Hz, 1H), 5.88 (d, J=8.2 Hz, 1H), 5.07 (m, 1H), 2.25-2.19 (m, 4H), 2.17 (s, 3H), 1.69 (s, 3H), 1.61 (s, 3H).

$^{13}$C-NMR (100 MHz, CDCl$_3$): δ 191.2, 163.7, 132.9, 127.4, 122.5, 40.6, 25.7, 25.6, 17.7, 17.5.

IR (neat, cm$^{-1}$): 1675, 1632, 1611.

MS m/z: 152 (M$^+$).

HRMS (EI); Calcd. for C$_{10}$H$_{16}$O: 152.1201, Found: 152.1199.

(s) Oxidation of 3-cyclohexene-1-methanol

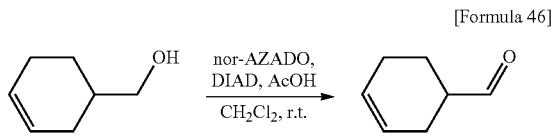

[Formula 46]

3-Cyclohexene-1-methanol (60.4 mg, 0.539 mmol) was oxidized in the same manner as that described in Example 8, (a) (except that Nor-AZADO was used at 3 mol %, and the reaction was performed at room temperature) to obtain the objective compound (48.1 mg; yield, 81.2%).

$^1$H-NMR (400 MHz, CDCl$_3$): δ 9.70 (d, J=0.97 Hz, 1H), 5.74-5.68 (m, 2H), 2.55-2.48 (m, 1H), 2.25-2.23 (m, 2H), 2.13-2.08 (m, 2H), 2.03-1.96 (m, 1H), 1.72-1.62 (m, 1H).

$^{13}$C-NMR (100 MHz, CDCl$_3$): δ 204.4, 127.2, 124.7, 46.0, 24.3, 23.7, 22.1.

IR (neat, cm$^{-1}$): 1729, 1652.

MS m/z: 110 (M$^+$).

HRMS (EI): Calcd. for C$_7$H$_{10}$O: 110.0732, Found: 110.0725.

(t) Oxidation of phenylpropynol

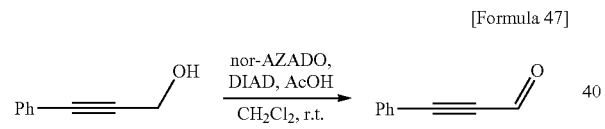

[Formula 47]

Phenylpropynol (51.6 mg, 0.390 mmol) was oxidized in the same manner as that described in Example 8, (a) (except that Nor-AZADO was used at 3 mol %, and the reaction was performed at room temperature) to obtain the objective compound (45.9 mg; yield, 90.4%).

$^1$H-NMR (400 MHz, CDCl$_3$): δ 9.43 (s, 1H), 7.62-7.59 (m, 2H), 7.51-7.47 (m, 1H), 7.43-7.39 (m, 2H).

$^{13}$C-NMR (100 MHz, CDCl$_3$): δ 176.7, 133.3, 131.3, 128.7, 119.5, 95.1, 88.4.

IR (neat, cm$^{-1}$): 2188, 1660, 759.

MS m/z: 130 (M$^+$).

HRMS (EI): Calcd. for C$_9$H$_6$O: 130.0419, Found: 130.0405.

(u) Oxidation of hydrobenzoin (1)

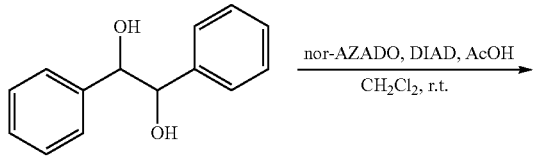

[Formula 48]

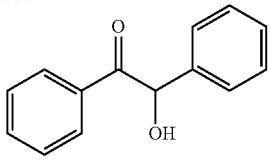

Hydrobenzoin (87.5 mg, 0.408 mmol) was oxidized in the same manner as that described in Example 8, (a) (except that Nor-AZADO was used at 3 mol %, and the reaction was performed at room temperature) to obtain the objective compound (76.7 mg; yield, 88.5%).

$^1$H-NMR (400 MHz, CDCl$_3$): δ 7.93-5.54 (m, 2H), 7.52-7.40 (m, 1H), 7.38-7.23 (m, 7H), 5.95 (d, J=6.3 Hz, 1H), 4.55 (d, J=6.3 Hz, 1H).

$^{13}$C-NMR (100 MHz, CDCl$_3$): δ 198.9, 139.0, 133.8, 133.5, 129.1, 129.1, 128.6, 128.5, 127.7, 76.2.

IR (neat, cm$^{-1}$): 3414, 1679.

MS m/z: 212 (M$^+$).

HRMS (EI): Calcd. for C$_{14}$H$_{12}$O$_2$: 212.0837, Found: 212.0829.

(v) Oxidation of hydrobenzoin (2)

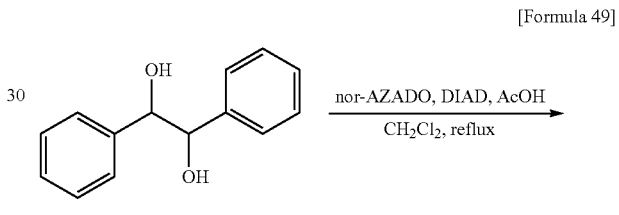

[Formula 49]

Hydrobenzoin (103.4 mg, 0.483 mmol) was oxidized in the same manner as that described in Example 8, (a) (except that Nor-AZADO was used at 3 mol %, and DIAD was used in an amount of 2 equivalents) to obtain the objective compound (93.4 mg; yield, 92.1%). The spectrum data were found to be the same as those obtained in Example 6, (k).

(w) Oxidation of 3-hydroxy-2,2,4-trimethylpentanol

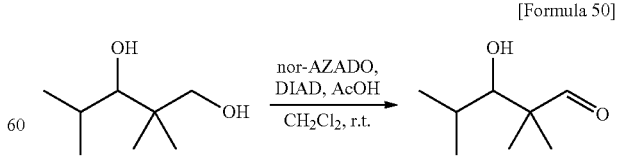

[Formula 50]

3-Hydroxy-2,2,4-trimethylpentanol (71.7 mg, 0.490 mmol) was oxidized in the same manner as that described in Example 8, (a) (except that Nor-AZADO was used at 3 mol %, and the reaction was performed at room temperature) to obtain the objective compound (58.7 mg; yield, 83.0%).

$^1$H-NMR (400 MHz, CDCl$_3$): δ 9.62 (s, 1H), 3.55 (dd, J=5.1, 4.1 Hz, 1H), 2.07 (brd, J=5.4 Hz, 1H), 1.92-1.84 (m, 1H), 1.12 (d, J=4.4 Hz, 6H), 0.97 (d, J=6.8 Hz, 3H), 0.90 (d, J=6.8 Hz, 3H).

$^{13}$C-NMR (100 MHz, CDCl$_3$): δ 206.7, 80.3, 50.5, 29.9, 21.7, 19.8, 18.6, 17.2.

IR (neat, cm$^{-1}$): 3479, 1714.

MS m/z: 145 (M$^+$+H).

HRMS (EI): Calcd. for C$_8$H$_{17}$O$_2$: 145.1229, Found: 145.1204.

INDUSTRIAL APPLICABILITY

According to the method of the present invention, even bulky secondary alcohol compounds can be efficiently oxidized, and the reaction can be efficiently performed with a smaller catalyst amount as compared with the conventional organic catalysts. Therefore, the method of the present invention is more advantageous than the conventional oxidization methods from industrial viewpoints, such as from viewpoints of economical efficiency and reaction efficiency. The method further enables efficient oxidization even with air as the bulk oxidant, and accordingly, the method can reduce the load on the environment.

What is claimed is:

1. A method for oxidizing an alcohol, wherein oxidation is performed in the presence of a compound represented by the following formula (I):

[Formula 1]

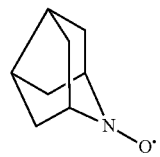

(I)

and a bulk oxidant.

2. The method according to claim 1, wherein the alcohol is a secondary alcohol.

3. The method according to claim 1, wherein the bulk oxidant is a peracid, hydrogen peroxide, a hypohalogen acid or a salt thereof, a perhalogen acid or a salt thereof, a persulfuric acid salt, a halogenating agent such as a halide and N-bromosuccinimide, a trihalogenated isocyanuric acid, a diacetoxyiodoallene, a dialkyl azodicarboxylate, oxygen, air, or a mixture thereof.

4. The method according to claim 1, wherein the bulk oxidant is air.

5. The method according to claim 2, wherein the bulk oxidant is a peracid, hydrogen peroxide, a hypohalogen acid or a salt thereof, a perhalogen acid or a salt thereof, a persulfuric acid salt, a halogenating agent such as a halide and N-bromosuccinimide, a trihalogenated isocyanuric acid, a diacetoxyiodoallene, a dialkyl azodicarboxylate, oxygen, air, or a mixture thereof.

6. The method according to claim 2, wherein the bulk oxidant is air.

7. The method according to claim 3, wherein the halogenating agent is a halide or N-bromosuccinimide.

8. The method according to claim 5, wherein the halogenating agent is a halide or N-bromosuccinimide.

* * * * *